(12) United States Patent
Receveur et al.

(10) Patent No.: US 8,744,548 B2
(45) Date of Patent: Jun. 3, 2014

(54) LEAD APPARATUS

(75) Inventors: Rogier Receveur, Maastricht (NL); Jean Joseph Gerardus Rutten, Bocholtz (NL); Karel F. A. A. Smits, Munstergeleen (NL); Nicolaas M Lokhoff, Kerkrade (NL); Sylvia Weijzen-Engels, Maastricht (NL); Didier Billy, Maastricht (NL); Tim Dirk Jan Jongen, Heerlen (NL); Lilian Kornet, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 757 days.

(21) Appl. No.: 12/795,236

(22) Filed: Jun. 7, 2010

(65) Prior Publication Data

US 2011/0024186 A1 Feb. 3, 2011

Related U.S. Application Data

(60) Provisional application No. 61/185,876, filed on Jun. 10, 2009.

(51) Int. Cl.
*A61B 5/042* (2006.01)
*A61N 1/05* (2006.01)

(52) U.S. Cl.
USPC .......................... 600/373; 607/122

(58) Field of Classification Search
USPC .................. 607/116, 122; 600/373
See application file for complete search history.

(56) References Cited

U.S. PATENT DOCUMENTS

| 4,892,102 | A | 1/1990 | Astrinsky |
| 6,052,607 | A | 4/2000 | Edwards et al. |
| 7,974,705 | B2 * | 7/2011 | Zdeblick et al. ............... 607/117 |
| 2008/0039916 | A1 | 2/2008 | Colliou et al. |
| 2008/0114230 | A1 * | 5/2008 | Addis ........................... 600/373 |

FOREIGN PATENT DOCUMENTS

EP  1 587 575 B1  10/2007

OTHER PUBLICATIONS

P0030437.02 (PCT/US2010/038075) PCT Notification of Transmittal of the International Search Report and the Written Opinion of the International Searching Authority.

* cited by examiner

*Primary Examiner* — Tammie K Heller
(74) *Attorney, Agent, or Firm* — Reed A. Duthler

(57) ABSTRACT

A lead including one or more electrodes having circuitry associated therewith. Each such electrode includes a circuit extending along and conforming to at least a portion of an inner surface of the electrode. The circuit includes an isolation substrate contacting at least a portion of the inner surface of the cylindrical electrode portion, a first contact electrically isolated from the electrode portion by the isolation substrate and an integrated circuit electrically coupled to the first contact and the electrode.

12 Claims, 28 Drawing Sheets

LEAD APPARATUS

CROSS-REFERENCE TO RELATED APPLICATIONS

This application claims the benefit of U.S. Provisional Application No. 61/185,876, filed on Jun. 10, 2009. The disclosure of the above application is incorporated herein by reference.

BACKGROUND

The disclosure herein relates generally to lead apparatus including one or more electrodes.

The medical device industry produces a wide variety of devices (e.g., pacemakers, defibrillators, neuro-stimulators, etc.) that utilize leads for treating a patient's medical conditions. Such leads often include one or more electrodes to contact a specific portion in the patient's body. Further, various leads have included electrodes incorporating electronics (e.g., see U.S. Pat. No. 6,473,653 issued on Oct. 29, 2002 and entitled "Selective Activation of Electrodes within Implantable Lead").

SUMMARY

The disclosure herein relates generally to a lead that includes one or more electrodes (e.g., intelligent electrodes, such as those having circuitry associated therein) that each includes a circuit portion and an electrode portion. Further, in one or more embodiments, such electrodes have the same physical characteristics as a conventional electrode (e.g., the presentation and location of the contacts of the electrode for use with known interconnection techniques, an opening extending through a central portion of the electrode, and/or stress-relief and stability characteristics).

One exemplary lead apparatus disclosed herein includes an elongated body and one or more electrodes located along the elongated body. For example, each electrode of the one or more electrodes may include a cylindrical electrode portion and a circuit portion. The cylindrical electrode portion may extend along an axis from a proximal end to a distal end and include a body-contacting outer surface and an inner surface. Further, the cylindrical electrode portion may include conductive material. Further, for example, the circuit portion may extend along and conform to at least a portion of the inner surface of the cylindrical electrode portion (e.g., defining at least a portion of an opening extending along the axis from the distal end to the proximal end of the cylindrical electrode portion). Further, the circuit portion may include an isolation substrate (e.g., a flexible substrate) contacting at least a portion of the inner surface of the cylindrical electrode portion, a first contact (e.g., at least partially located beyond the proximal end of the cylindrical electrode portion) electrically isolated from the cylindrical electrode portion by the isolation substrate, a second contact (e.g., at least partially located beyond the proximal end of the cylindrical electrode portion) electrically isolated from the cylindrical electrode portion by the isolation substrate, and an integrated circuit (e.g., a flexible integrated circuit) electrically coupled to the first contact, the second contact, and the cylindrical electrode portion. Further, the lead may include one or more conductors (e.g., a coil conductor and/or a cable conductor) to electrically couple each of the one or more electrodes.

Another exemplary lead apparatus disclosed herein includes an elongated body and one or more electrodes located along the elongated body. For example, each electrode of the one or more electrodes may include a cylindrical electrode portion and a circuit portion. The cylindrical electrode portion may extend along an axis from a proximal end to a distal end and may include a body-contacting outer surface and an inner surface. Further, the cylindrical electrode portion may include conductive material. Further, for example, the circuit portion may extend along at least a portion of the inner surface of the cylindrical electrode portion between at least the proximal end and the distal end. Further, the circuit portion may include an isolation substrate contacting at least a portion of the inner surface of the cylindrical electrode portion, a first contact electrically isolated from the cylindrical electrode portion by the isolation substrate, a second contact electrically isolated from the cylindrical electrode portion by the isolation substrate, and an integrated circuit electrically coupled to the first contact, the second contact, and the cylindrical electrode portion. Further, the circuit portion may define at least a portion of an opening extending along the axis of the cylindrical electrode portion from the distal end to the proximal end. The first contact may include a first arcuate contact surface and the second contact may include a second arcuate contact surface. Further, at least the first arcuate contact surface of the first contact and the second arcuate contact surface of the second contact of the circuit portion of the one or more electrodes may face in a direction towards (or away from) the axis.

Another exemplary lead apparatus disclosed herein includes an elongated body, at least one conductor extending along at least a portion of the elongated body, and one or more electrodes located along the elongated body. For example, each electrode of the one or more electrodes may include a cylindrical electrode portion and a circuit portion. The cylindrical electrode portion may extend along an axis from a proximal end to a distal end and may include a body-contacting outer surface and an inner surface. Further, the cylindrical electrode portion may include conductive material. Further, for example, the circuit portion may extend along and conform to at least a portion of the inner surface of the cylindrical electrode portion between at least the proximal end and the distal end. Further, the circuit portion may include an integrated circuit (e.g., a flexible integrated circuit) capacitively couplable to the cylindrical electrode portion and the at least one conductor, a first isolation layer (e.g., a flexible substrate) contacting at least a portion of the inner surface of the cylindrical electrode portion and the integrated circuit to electrically isolate the integrated circuit and the cylindrical electrode portion, and a second isolation layer (e.g., a flexible substrate) contacting at least a portion of the at least one conductor and the integrated circuit to electrically isolate the integrated circuit and the at least one conductor. Further, the circuit portion may include at least two capacitive structures electrically coupled to the integrated circuit, and each of the at least two capacitive structures may be for capacitively coupling the integrated circuit to one of the cylindrical electrode portion and the at least one conductor. Still further, the circuit portion may include at least one shield structure for electromagnetically shielding the integrated circuit (e.g., from parasitic signals), and each of the at least one shield structure may be located between the integrated circuit and one of the at least two capacitive structures.

One exemplary ring electrode disclosed herein includes a cylindrical electrode portion and a circuit portion. For example, the cylindrical electrode portion may extend along an axis from a first end to a second end and may include a body-contacting outer surface and an inner surface. Further, the cylindrical electrode portion may include conductive material. Further, for example, the circuit portion may extend along and conform to at least a portion of the inner surface of the cylindrical electrode portion. Further, the circuit portion may include an isolation substrate (e.g., a flexible substrate) contacting at least a portion of the inner surface of the cylindrical electrode portion, a first contact electrically isolated from the cylindrical electrode portion by the isolation substrate, a second contact electrically isolated from the cylindrical electrode portion by the isolation substrate, and an integrated circuit (e.g., a flexible integrated circuit) electrically coupled to the first contact, the second contact, and the cylindrical electrode portion. The second contact may include a second arcuate contact surface and the first contact may include a first arcuate contact surface.

One exemplary method of manufacturing a ring electrode disclosed herein includes providing a cylindrical electrode portion, providing at least a circuit portion in a planar configuration, and coupling the circuit portion to the cylindrical electrode. For example, the cylindrical electrode portion may include at least conductive material and may extend along an axis from a first end to a second end. Further, the cylindrical electrode portion may include a body-contacting outer surface and an inner surface defining a cylindrical electrode opening extending along the axis from the first end to the second end. Further, for example, the circuit portion may include a flexible isolation substrate for contacting at least a portion of the inner surface of the cylindrical electrode portion when the circuit portion is inserted into the opening of the cylindrical electrode portion, a first contact, a second contact, and an integrated circuit electrically coupled to the first contact and the second contact. Still further, for example, coupling the circuit portion to the cylindrical electrode may include coupling the circuit portion within the cylindrical electrode opening of the cylindrical electrode portion (e.g., welding a flange portion of the circuit portion to the second end of the cylindrical electrode portion, welding at least one tongue of the circuit portion within at least one aperture of the cylindrical electrode portion, etc.).

Further, for example, coupling the circuit portion within the cylindrical electrode opening of the cylindrical electrode portion may include deflecting the circuit portion from the planar configuration, inserting the circuit portion into the cylindrical electrode opening of the electrode portion such that the circuit portion conforms along at least a portion of the inner surface of the cylindrical electrode portion (wherein the first and the second contacts of the circuit portion are electrically isolated from the cylindrical electrode portion), mechanically coupling the circuit portion to the cylindrical electrode portion (e.g., welding a portion of the circuit portion to a portion of the cylindrical electrode portion), and electrically coupling the integrated circuit of the circuit portion to the cylindrical electrode portion, the first contact, and the second contact.

The above summary is not intended to describe each embodiment or every implementation of the lead. A more complete understanding will become apparent and appreciated by referring to the following detailed description and claims taken in conjunction with the accompanying drawings.

Figure 1:
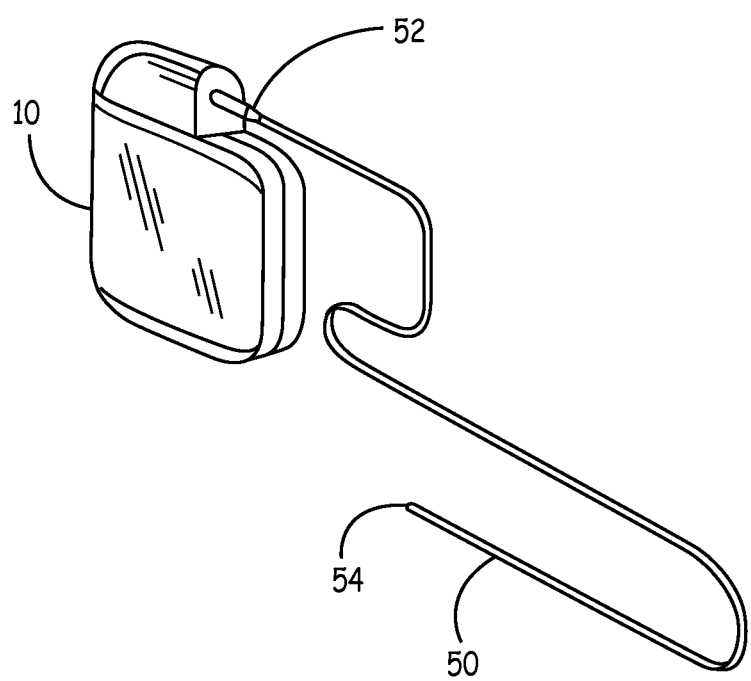
FIG. 1 is a perspective view of an exemplary lead attached to a device.

The figures are rendered primarily for clarity and, as a result, are not necessarily drawn to scale.

DETAILED DESCRIPTION OF EXEMPLARY EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary apparatus, and methods of constructing such apparatus, shall generally be described with reference to FIGS. 1-27. It will be apparent to one skilled in the art that elements from one embodiment may be used in combination with elements of the other embodiments, and that the possible embodiments of such apparatus using combinations of features set forth herein is not limited to the specific embodiments shown in the FIGS. and/or described herein. Further, it will be recognized that the embodiments described herein will include many elements that are not necessarily shown to scale. Still further, it will be recognized that the size and shape of various elements herein may be modified without departing from the scope of the present disclosure, although one or more shapes and sizes, or types of elements, may be advantageous over others.

FIG. 1 shows a perspective view of an exemplary lead 50 attached to a device 10. The device 10 may be a pacemaker, defibrillator, neuro-stimulator, and/or any medical device capable of utilizing the lead 50. The lead 50 may extend from a proximal end 52 coupled to the device 10 to a distal end 54. At least a portion of the lead 50 may be implanted into the body of a patient to, e.g., deliver therapy, monitor the body, etc.

Figure 2:
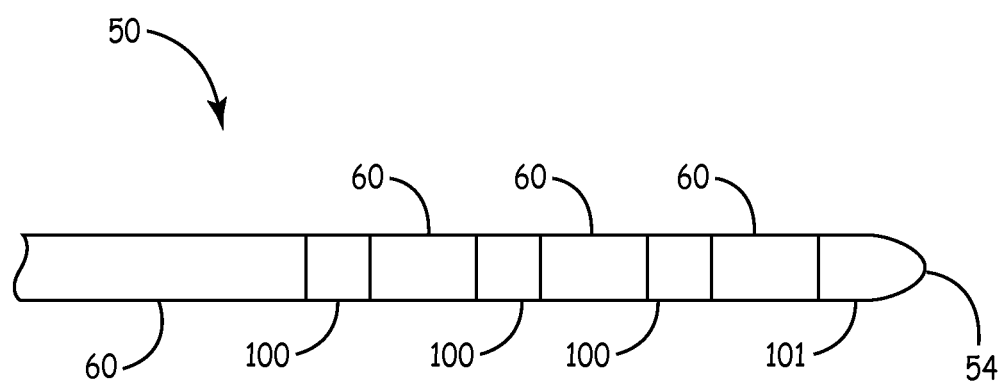
FIG. 2 is a partial-side view of the lead of FIG. 1 including multiple electrodes.
Figure 3:
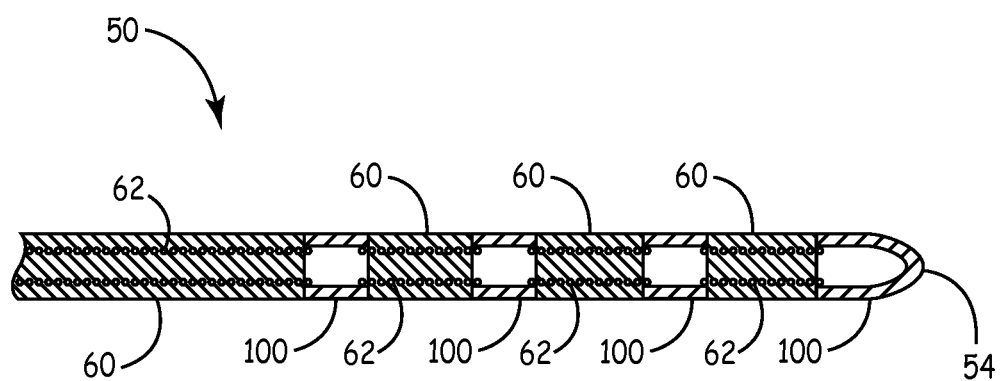
FIG. 3 is a cross-sectional side view of the lead of FIG. 2.

A partial side-view of the lead 50 is shown in FIG. 2 and a cross-sectional view of the lead 50 of FIG. 2 is shown in FIG. 3. The lead 50 includes an elongated lead body 60. Lead body 60 may include one or more conductors 62 (e.g., insulated elongated conductive elements) and one or more electrodes 100 that may be located along the length of the lead body 60, e.g., towards the distal end of the lead body 60, etc. In at least one embodiment, lead body 60 may position the one or more electrodes 100 with respect to various cardiac locations so that device 10 can deliver electrical stimuli to appropriate locations in the cardiac space. For example, multiple electrodes 100 may be located along the length of the lead body 60 between portions of the lead body 60 with a tip electrode 101 located at the distal end 54. Further, the elongated lead body 60 may include monolumen and multilumen tubing configurations and may be formed of any suitable material or materials and of any number of components. For example, the lead body 60 may be formed, at least in part, of silicone rubber, polyurethane, fluoropolymers, Pursil (poly urethane silicon mixture), and/or any other suitable material.

The lead body 60 includes the one or more conductors 62 (e.g., insulated elongated conductive elements) that extend from the device 10 of FIG. 1 to the one or more electrodes 100 or any other device located along or within the lead body 60 (e.g., to electrically couple the one or more electrodes 100 or other devices to the device 10). The conductors 62 may be stranded, braided, coil wound around a filament, or solid wire and may be provided in any configuration, e.g., linear or helical coil arrangements. Further, the conductors may be formed of, e.g., MP35N, silver drawn filled tubing (Ag-DFT), MP35N with a silver core, platinum, nickel, cobalt, magnesium, iridium, gold, silver, titanium, nitinol, palladium, tantalum, tungsten, and/or alloys thereof. Still further, the conductors 62 may be electrically insulated by any material capable of electrically insulating the conductors 62, for example, a polymer (e.g., ethylene tetrafluoroethylene (ETFE), polytetrafluoroethylene (PTFE), silicone rubber, and/or polyurethane).

As used herein, a "cable conductor" is defined as a conductor extending substantially linearly (e.g., a linear arrangement). Further, as used herein, a "coil conductor" is defined as a conductor wound (e.g., spirally) in a series (e.g., continuous series) of loops (e.g., a helical coil arrangement). The one or more conductors 62 shown in FIG. 3 may be coil or cable conductors.

As depicted, the lead 50 includes multiple ring electrodes 100. The lead 50, however, may include electrodes of any size, shape, and/or type. For example, the lead 50 may include electrodes that do not wrap around the entire lead 50 (e.g., a partial ring). Further, the electrodes 100 may be pacing electrodes (e.g., shocking electrodes) and/or sensors (e.g., pressure sensors, electrical sensors, etc.).

The conductors 62 may be electrically coupled to the electrodes 100, 101 in various ways. For example, the conductors 62 may be welded (e.g., laser welded), crimped, and/or staked to a portion (e.g., an inside surface, a flange of the electrode, etc.) of each of the electrodes 100, 101.

Figure 4:
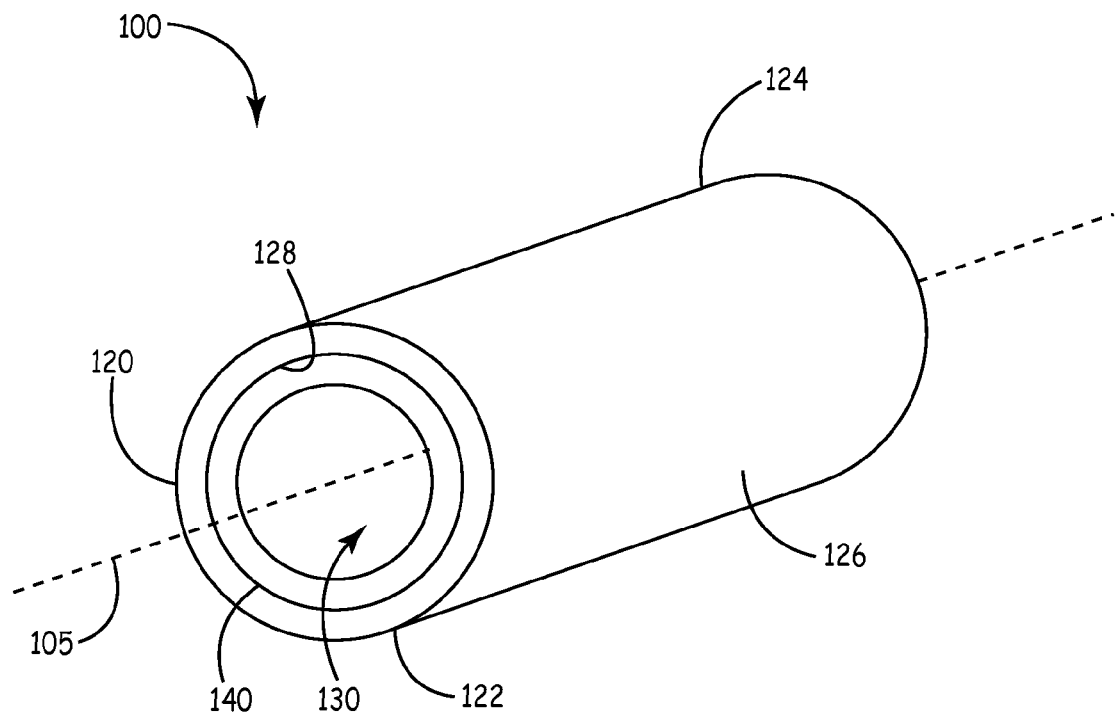
FIG. 4 is a perspective view of an exemplary electrode of the lead of FIG. 2.

A perspective view of the exemplary electrode 100 (e.g., an intelligent electrode) of the lead 50 of FIG. 2 is shown in FIG. 4. The electrode 100 includes a cylindrical electrode portion 120 and a circuit portion 140. Although the electrode portions described herein are described as being cylindrical, in one or more embodiments, the electrode portions may be any other flat or three-dimensional shape that may be used in an electrode, e.g., partial segments of a cylinder, oval tubes, flat-square tubes, flat-round, etc.

The cylindrical electrode portion 120 extends along an axis 105 from a proximal end 122 to a distal end 124 and includes a body-contacting outer surface 126 and an inner surface 128. When the lead 50 is inserted into a body portion, the body-contacting outer surface 126 is the portion of the electrode 100 that contacts the body of the patient. The cylindrical electrode portion 120 includes one or more conductive materials, e.g., platinum, iridium, sputtered platinum, gold, silver, titanium, nitinol, tantalum, tungsten, and/or alloys thereof. Further, the cylindrical electrode portion 120 may be a single portion (e.g., a cylinder) or two or more portions (e.g., two half cylinders that are joined together). Still further, the cylindrical electrode portion 120 may include one or more portions, each of which may define a portion of the circumference of the cylindrical electrode portion 120 (e.g., a portion may be 10%, 25%, 33%, 40%, 50%, 66%, or 75% of the circumference of the cylindrical electrode portion 120).

In at least one embodiment, only about one half of the electrode 100 is utilized for connections/electronics (e.g., one half of the cylinder), which, e.g., may ease the production of electrodes including intelligence. Further, conductors may be connected to one side of the electrode 100 via standard connections methods. In other words, the electrode 100 includes multiple metal-containing layers (e.g., the cylindrical electrode portion 120 and the circuit portion 140) isolated from each other as opposed to a conventional electrode that may include a single layer of metal.

Further, in at least one embodiment, the electrode 100 is split-up in two parts for assembly reasons. After assembly, the cylindrical electrode portion 120 (e.g., the interface to the tissue) is not split radially, it is again one closed electrical entity. The circuit portion 140 (e.g., that is electrically isolated from the outer portion) is split-up radially in two parts because the circuit portion may use two poles "+" and "−"to function.

The circuit portion 140 includes circuitry to provide certain functionally described herein (e.g., intelligence to the electrode, such as switchable electrode functionality, signal conditioning close to the electrode, and/or stimulation pulse generation at the electrode). In at least one embodiment, the circuit portion 140 (and/or any other portion of the electrode 100) may utilize molded interconnect device techniques, folding flat flexible electronics, flexible integrated circuits, polymer electronics, conventional silicon chip with appropriate form factor, thinned silicon, and/or system in package technology to, e.g., implement the electrode structure, circuit portion, etc. Further, the circuit portion 140 (and/or any portion or component of the circuit portion 140) may be flexible.

As used herein, "flexible" is defined as being deflectable from a normal state (e.g., deviating from a previous position). For example, a flexible circuit portion 140 may be planar in a normal state and may be deflected (e.g., permanently or temporarily) from such plane (e.g., into a curved shaped) in an abnormal state. Further, the circuit portion 140 is combined with the cylindrical electrode portion 120 to form the electrode 100 such that it appears to be a conventional electrode. For example, the circuit portion 140 extends along and conforms to at least a portion of the inner surface 128 of the cylindrical electrode portion 120 between at least the proximal end 122 and the distal end 124. The circuit portion 140 may conform to the inner surface 128 of the cylindrical electrode portion 120 by adjusting to the shape of the inner surface 128 such that the circuit portion 140 fits in close proximity with the inner surface 128 (e.g., the circuit portion 140 may bend into a shape that fits adjacent and/or flush to the inner surface 128 thereby presenting an interior volume (e.g., a volume in the interior of the lead body enclosed by various components of the lead body such as, e.g., insulation materials of the mono-lumen and multi-lumen tubing configurations) similar to a conventional electrode (e.g., the contacts may be located within the interior volume in substantially the same locations as the contacts included in a conventional electrode, the interior volume may be the same size and/or shaped as the interior volume of a conventional electrode, etc.). In one or more embodiments, the circuit portion 140 extends along the entire circumference of the inner surface 128 of the cylindrical electrode portion 120. Further, in one or more embodiments, the circuit portion 140 includes one or more portions, each of which may extend along a portion of the circumference of the inner surface 128 of the cylindrical electrode portion 120 (e.g., the portion may be 10%, 25%, 33%, 40%, 50%, 66%, 75%, or 90% of the circumference of the inner surface 128 of the cylindrical electrode portion 120). Still further, in one or more embodiments, the circuit portion 140 may extend along a portion of the longitudinal length (i.e., from the proximal end 122 to the distal end 124) of the cylindrical electrode portion 120 (e.g., the portion may be 10%, 25%, 33%, 40%, 50%, 66%, 75%, or 90% of the length of the cylindrical electrode portion 120) or may extend past/beyond the longitudinal length of the cylindrical electrode portion 120 (e.g., 110%, 125%, 133%, 140%, 150%, 166%, 175%, or 190% of the length of the cylindrical electrode portion 120). Yet still further, in one or more embodiments, the circuit portion 140 may include one or more isolation portions and/or one or more integrated circuit portions described further herein with respect to electrode 200 of FIGS. 5-10.

The circuit portion 140 defines at least a portion of an opening 130 extending along the axis 105 from the proximal end 122 to the distal end 124 of the cylindrical electrode portion 120 to allow, e.g., other devices such as guide wires, stylets, conductors, etc. to extend therethrough. Further, although not depicted in FIG. 4, the circuit portion 140 may include contacts that present arcuate contact surfaces (e.g., arcuate contact surfaces facing in a direction towards axis 105 or facing in a direction away from axis 105). As used herein, the term "arcuate contact surface" is defined as a contact surface curved about one axis. Such arcuate contact surface may include circular arcuate surfaces.

An exemplary electrode 200 is depicted in FIGS. 5-10. The electrode 200 includes a cylindrical electrode portion 220 and a circuit portion 240 that may be similar to the cylindrical electrode portion 120 and the circuit portion 140 of the electrode 100 of FIG. 4 as described herein, and as such, may share some of the same characteristics and/or features.

The cylindrical electrode portion 220 extends along an axis 205 from a proximal end 222 to a distal end 224 and includes a body-contacting outer surface 226 and an inner surface 228. When a lead including electrode 200 is inserted into a body portion, the body-contacting outer surface 226 is the portion of the electrode 200 that contacts the body of the patient.

The circuit portion 240 is combined with the cylindrical electrode portion 220 to form the electrode 200 such that it appears to be a conventional electrode. For example, the circuit portion 240 extends along and conforms to at least a portion of the inner surface 228 of the cylindrical electrode portion 220 (e.g., between at least the proximal end 222 and the distal end 224). Further, the circuit portion 240 defines at least a portion of an opening 230 extending along the axis 205 from the proximal end 222 to the distal end 224 of the cylindrical electrode portion 220 to allow, e.g., other devices, such as conductors, guide wires, etc. to extend therethrough.

The circuit portion 240 in one embodiment includes two portions: a first half 242 and a second half 244. In one embodiment depicted in FIGS. 5-10, first half 242 includes various components of the circuit portion 240 while the second half 244 is formed of other material, such as insulative material and does not include any other functionally relevant components. The insulative material of the second half 244 may be formed of any material capable of electrically insulating the circuit portion 240, electrode portion 220, etc. For example, insulative material can include a polymer. Exemplary material can include hard (anti-static) plastic, ethylene tetrafluoroethylene (ETFE), polytetrafluoroethylene (PTFE), silicone rubber, and/or polyurethane. In one or more embodiments, the second half 244 may include various other functional components (e.g., that provide intelligence to the electrode), such as the components of the first half 242 described herein. Further, in one or more embodiments, the circuit portion 240 is a single portion or may be split into more than two portions.

In one embodiment, the first half 242 of the circuit portion 240 includes an isolation substrate 250, a first contact 260, a second contact 262, and an integrated circuit 270. The isolation substrate 250 contacts at least a portion of the inner surface 228 of the cylindrical electrode portion 220 to electrically isolate other components (e.g., the first contact 260 and the second contact 262) from the cylindrical electrode portion 220. As used herein, "electrically isolate" is defined as separating a first item from physical electrical connection with a second item.

Further, the isolation substrate 250 includes an opening 252 within which the integrated circuit 270 may be located. In other embodiments, the isolation substrate 250 may not include the opening 252 and may be directly coupled to or abut the integrated circuit 270. Still, further, the isolation substrate 250 may be formed of, e.g., a flexible substrate, a flexible printed circuit board (PCB), hard (anti-static) plastic, ethylene tetrafluoroethylene (ETFE), polytetrafluoroethylene (PTFE), silicone rubber, and/or polyurethane.

In or more embodiments, the first contact 260 and the second contact 262 are located proximate the proximal end 222 and electrically isolated from the cylindrical electrode portion 220 by the isolation substrate 250. The circuit portion 240 may further include a third contact 264 and a fourth contact 266 located proximate the distal end 224 and also electrically isolated from the cylindrical electrode portion 220 by the isolation substrate 250.

The third contact 264 is electrically coupled to the first contact 260 and the fourth contact 266 is electrically coupled to the second contact 262 (e.g., such as by an electrical trace formed on, in, or along the isolation substrate 250). In the embodiment depicted, the third contact 264 is integral with the first contact 260 and the second contact 262 is integral with the fourth contact 266 (e.g., such contacts are as part of a trace formed on, in, or along the isolation substrate 250). As such, electrically coupling of the first contact 260 to the third contact 264 and the second contact 262 to the fourth contact 266 is achieved. In one or more embodiments, a connector (e.g., a cable conductor) may electrically couple the first contact 260 to the third contact 264 and second contact 262 to the fourth contact 266. The first, second, third, and fourth contacts 260, 262, 264, 266 are formed of a conductive material, e.g., platinum, iridium, titanium, copper, silver, gold, nickel, aluminum, nitinol, tantalum, tungsten, and/or alloys thereof.

Further, the first, second, third, and fourth contacts 260, 262, 264, 266 may include first, second, third, and fourth arcuate contact surfaces 261, 263, 265, 267, respectively, facing in a direction towards the axis 205 for connection to one or more conductors (e.g., a coil conductor). In one or more embodiments, a portion of a conductor is welded (e.g., laser welded), crimped, and/or staked to each of the arcuate contact surfaces 261, 263, 265, 267.

The first, second, third, and fourth contacts 260, 262, 264, 266 may have a thickness 294 (see FIG. 9) of about 25 microns to about 60 microns (e.g., 50 microns). In one or more embodiments, the contacts 260, 262, 264, 266 or at least a portion of the contacts 260, 262, 264, 266 are formed from bulk material (e.g., stamped, molded, machined, etc.). Further, in one or more embodiments, the contacts 260, 262, 264, 266 are formed using a deposition process. An exemplary deposition process is sputtering; however, it is understood that other methods can be used to form contacts 260, 262, 264, 266. Still further, in one or more embodiments, a portion of the contacts 260, 262, 264, 266 may be formed using a deposition process (e.g., the portion adjacent the isolation substrate 250) and another portion of the contacts 260, 262, 264, 266 may be formed from bulk material (e.g., the portion that presents the arcuate contact surfaces 261, 263, 265, 267).

Figure 10:
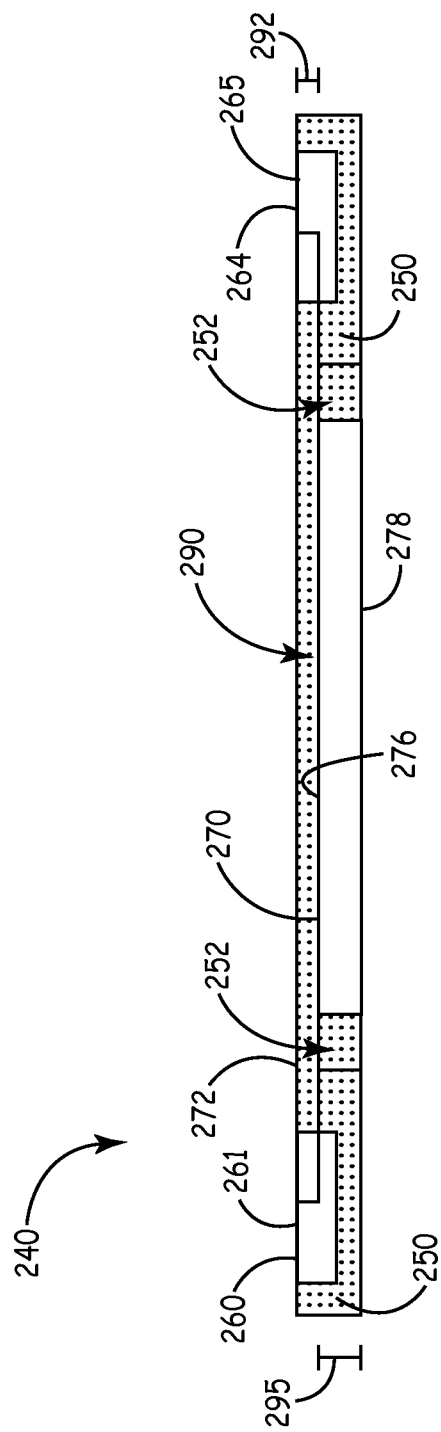
FIG. 10 is a cross-sectional view of the circuit portion of FIG. 8 taken along line 10-10.

The integrated circuit 270 of the circuit portion 240 may be located in the opening 252 defined within the isolation substrate 250 and may include a first surface 276 and a second surface 278 (see FIG. 10). Further, the integrated circuit 270 includes circuitry that may be utilized to perform a variety of functions. In one or more embodiments, the integrated circuit 270 is operable as a switch to "activate" or "disable" the electrode 200 and/or the integrated circuit 270 is operable as a signal conditioning function to improve signal/noise conditions. The integrated circuit 270 is electrically coupled to the first contact 260 with connector 272 and the second contact 262 with connector 274 to receive signals from, e.g., conductors electrically coupled to the first contact 260 and the second contact 262 that may extend to a medical device, e.g., device 10 of FIG. 1. In one or more embodiments, the connectors 272, 274 may be laser ribbon bonded to the contacts 260, 262, respectively. For example, the first contact 260 may receive a control signal from the device 10 to provide instructions to the integrated circuit 270 and the second contact 262 may receive a pulse signal from the device to deliver to the electrode portion 220.

Further, the integrated circuit 270 may be electrically coupled to the cylindrical electrode portion 220 to, e.g., deliver electrical pulses to the body of the patient, sense electrical signals from the body of the patient, etc. The integrated circuit 270 may be electrically coupled to the cylindrical electrode portion 220 in a variety of ways. For example, the integrated circuit 270 may include a backside contact located on the second surface 278 for electrical connection to the inner surface 228 of the cylindrical electrode portion 220 (see, e.g., FIG. 21). Further, for example, the integrated circuit 270 may include an electrode connector (e.g., a cable conductor) electrically coupling the integrated circuit 270 (e.g., a contact located on the first surface 276 or the second surface 278) to the cylindrical electrode portion 220. Still further, for example, the integrated circuit 270 may be separated from the cylindrical electrode portion 220 by a dielectric material that permits a capacitive coupling between the integrated circuit 270 and the cylindrical electrode portion 220 (see, e.g., FIGS. 24-27).

In at least one embodiment, each contact 260, 262 acts as an input to the integrated circuit 270 and the cylindrical electrode portion 220 acts at an output from the integrated circuit 270. For example, the integrated circuit 270 may operate as a controllable switch network (e.g., controllable by a processor or controller of the device 10) that is capable of selectively electrically coupling the first contact 260 to the cylindrical electrode portion 220, coupling the second contact 262 to the cylindrical electrode portion 220, and/or not coupling either of contacts 260, 262 to the cylindrical electrode portion 220. Further, in at least one embodiment, each contact 260, 262 acts as an output (or contact 260 as an input and contact 262 as an output) to the integrated circuit 270 and the cylindrical electrode portion 220 acts at an input from the integrated circuit 270.

Figure 8:
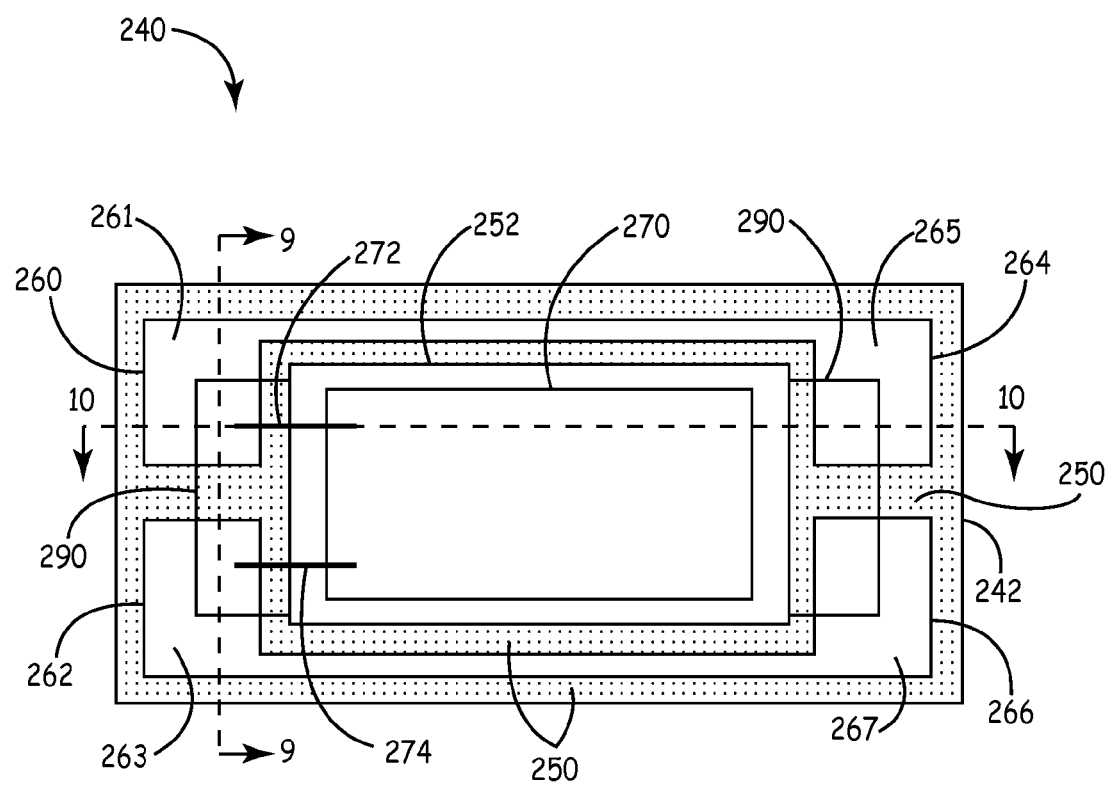
FIG. 8 is a top-plan view of a circuit portion of the electrode of FIG. 5.
Figure 9:
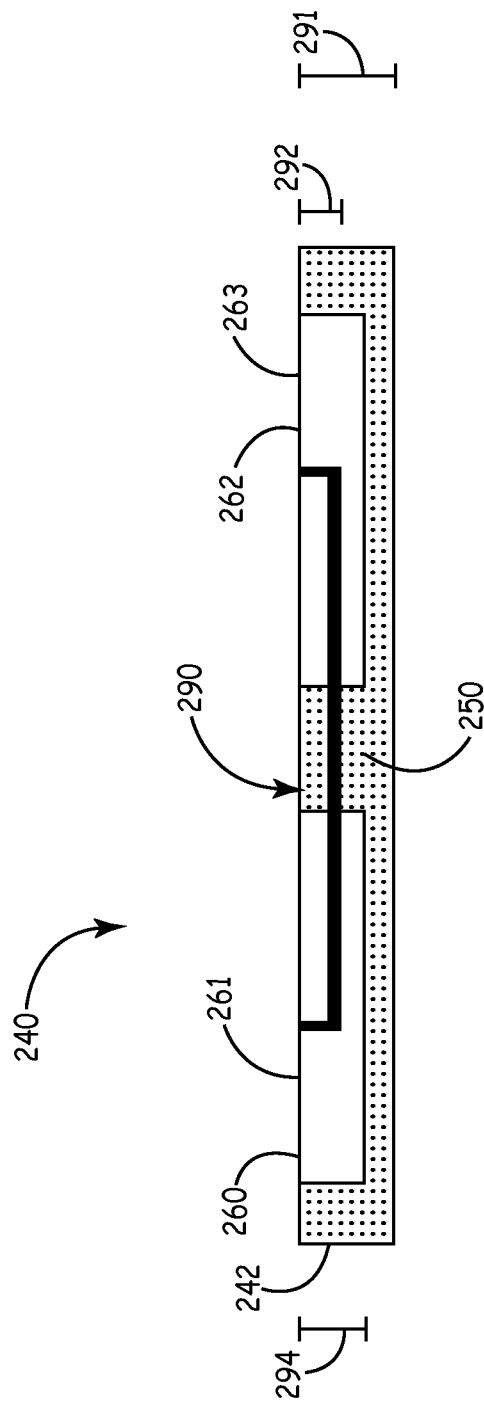
FIG. 9 is a cross-sectional view of the circuit portion of FIG. 8 taken along line 9-9.

In one or more embodiments, the circuit portion 240 (including the integrated circuit 270 and/or the isolation substrate 250) is flexible, e.g., to conform to at least a portion of the inner surface 228 of the cylindrical electrode portion 220. Further, in one or more embodiments, only the integrated circuit 270 is flexible while the remainder of the circuit portion 250 may be inflexible. Further, in one or more embodiments, only the isolation substrate 250 is flexible while the remainder of the circuit portion 250 may be inflexible. Before being located within (or after removal from) the cylindrical electrode portion 220, the circuit portion 240 may be substantially planar (e.g., the circuit portion 240 or at least a portion of the circuit portion 240 may be provided as substantially planar). For example, when manufacturing the electrode 200, the circuit portion 240 may be deflected from the planar configuration, inserted into the cylindrical electrode opening 230 of the cylindrical electrode portion 220 such that the circuit portion 240 conforms along at least a portion of the inner surface 228 of the cylindrical electrode portion 220, mechanically coupled to the cylindrical electrode portion 220, and electrically coupled to the cylindrical electrode portion 220, the first contact 260, and the second contact 262. A top-plan view of the circuit portion 240 of the electrode 200 of FIG. 5 in a substantially planar configuration is depicted in FIG. 8. Further, a cross-sectional view of the circuit portion 240 of FIG. 8 taken along line 9-9 is shown in FIG. 9 and a cross-sectional view of the circuit portion 240 of FIG. 8 taken along line 10-10 is shown in FIG. 10. From these views, some features of the circuit portion 240 may be more clearly shown.

For example, the circuit portion 240 may include a secondary opening 290 (see, e.g., FIGS. 8-9) extending into the circuit portion 240 to, e.g., position a portion of the contacts 260, 262, 264, 266 at the same thickness as the integrated circuit 270. The connectors (e.g., connector 272) may be electrically coupled to the contacts (e.g., contact 260) within the secondary opening 290. In this embodiment, the thickness of 292 of the secondary opening 290 is equal to the thickness 291 of entire circuit portion 240 minus the thickness 295 of the integrated circuit 270 (see FIGS. 9-10). In other embodiments, however, the secondary opening 290 may be less than, greater than, or equal to the thickness 291 of the entire circuit 240 minus the thickness 295 of the integrated circuit 270. In other words, the contact surfaces 261, 263, 265, 267 may be located lower than, higher than, or the same height as the integrated circuit 270. Further, in at least one embodiment, the secondary opening 290 and thicknesses of the components and/or portions of the circuit portion 240 may be sized such that the connectors (e.g., connector 272) do not extend above (or outside of) the contacts 261, 263, 265, 267. Still further, in at least one embodiment, the circuit portion 240 does not include a secondary opening 290.

Figure 11:
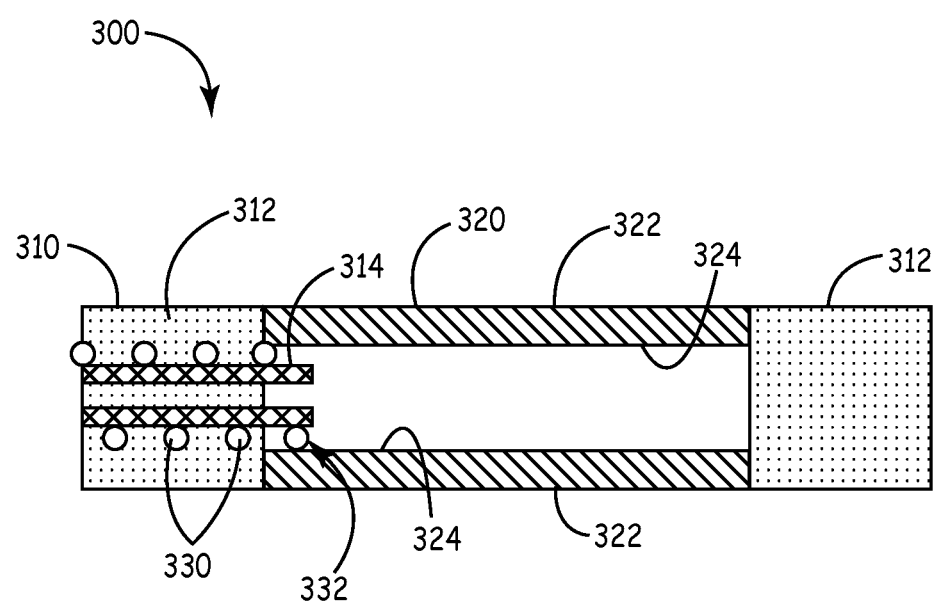
FIG. 11 is a longitudinal cross-sectional view of a portion of a lead including a conventional electrode.

A cross-sectional view of a portion 300 of a lead 310 including a conventional ring electrode 320 is shown in FIG. 11. The conventional ring electrode 320 includes a body-contacting surface 322 and an arcuate inner surface 324. A coil conductor 330 is shown extending through the lead body 312 and is electrically coupled to the inner arcuate contact surface 324 of the ring electrode 320 at location 332. In this embodiment, the coil conductor 330 is crimped between structure 314 and the arcuate inner surface 324 of the ring electrode 320. In other leads, the coil or cable conductors may be welded (e.g., laser welded), crimped, and/or staked to the arcuate inner surface 324 of the ring electrode 320. In other conventional electrodes, the conductors may be coupled to other portions of the electrodes, e.g., outer surfaces (see FIG. 16), circular openings (see FIG. 22), etc.

Figure 5:
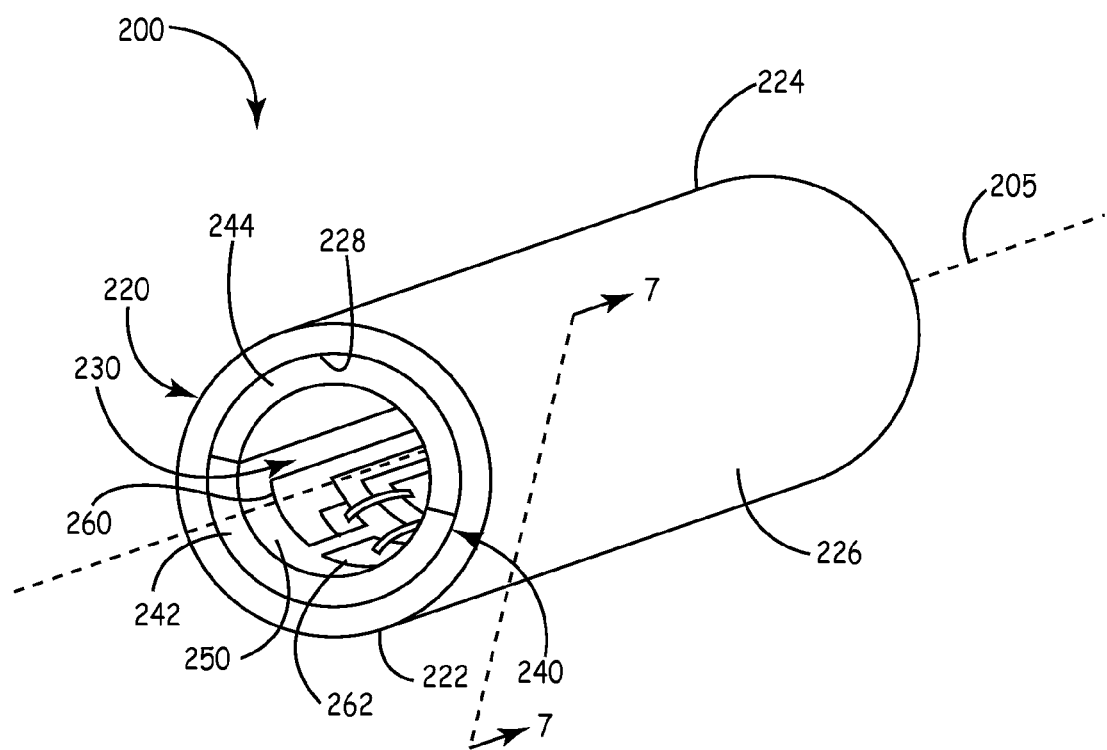
FIG. 5 is a detailed perspective view of another exemplary electrode.
Figure 6:
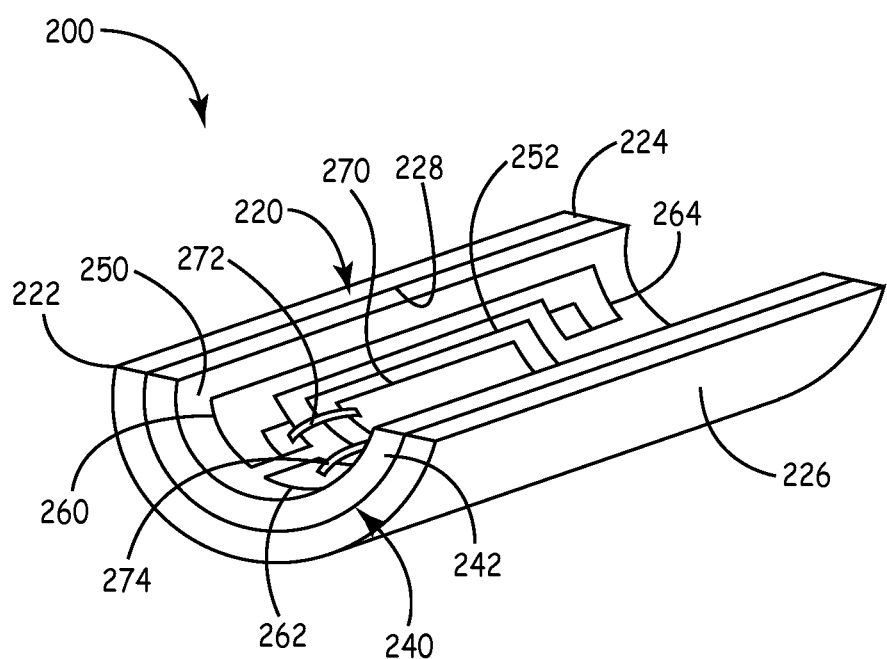
FIG. 6 is a partial perspective view of the electrode of FIG. 5.
Figure 7:
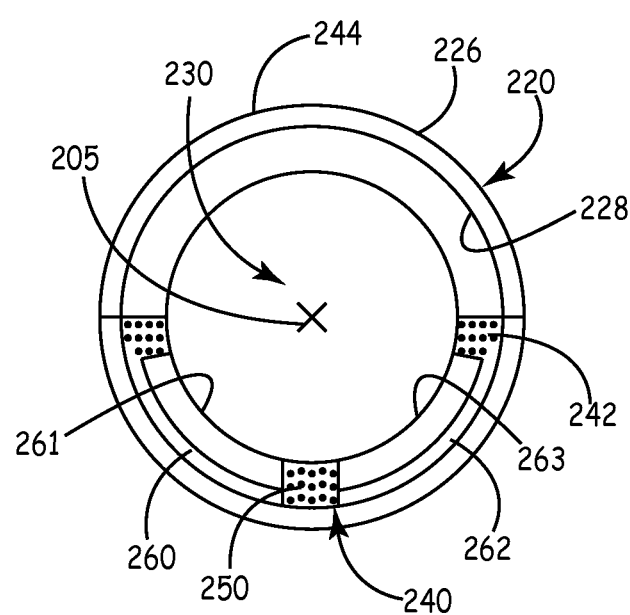
FIG. 7 is a cross-sectional view of the electrode of FIG. 5 taken along line 5-5.
Figure 12:
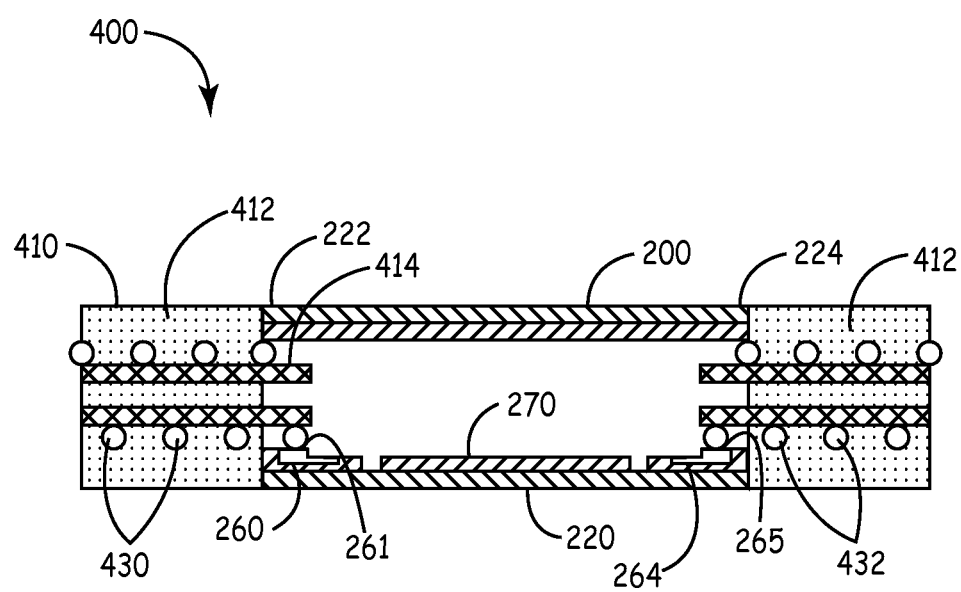
FIG. 12 is a longitudinal cross-sectional view of a portion of an exemplary lead including the electrode of FIG. 5.

A cross-sectional view of a portion 400 of an exemplary lead 410 including the electrode 200 of FIG. 5 is shown in FIG. 12. Comparing electrode 320 as shown in FIG. 11 with electrode 200 of FIG. 12 shows, in part, how the electrode 200 has some of the same physical characteristics and/or same presentation as a conventional electrode.

As shown, a first coil conductor 430 extends through the lead body 412 and is electrically coupled to the first arcuate contact surface 261 of the first contact 260 proximate the proximal end 222 of the electrode 200. Similar to the lead 310 of FIG. 11, the coil conductor 430 is crimped between support structure 414 and the first arcuate surface 261 of the first contact 260 the electrode 200. In other leads, however, the conductors may be electrically coupled to the first contact 260 in substantially any other suitable manner (e.g., weld).

Further, a second coil conductor 432 is electrically coupled to the third arcuate contact surface 265 of the third contact 264 proximate the distal end 224 of the electrode 200. Because the first contact 260 and the third contact 264 are electrically coupled (e.g., in this embodiment, the first contact 260 and the third contact 264 are coupled as part of a trace formed on the isolation substrate 250), the first coil conductor 430 is electrically coupled to the second coil conductor 432. As a result, the conductors 420, 432 effectively form a single conductor.

Although not shown, all the electrodes of the lead 410 may have similar connections. For example, the second coil conductor 432 may extend to another electrode substantially similar to electrode 200 and be electrically coupled to the first contact of that electrode. As a result, the first contacts (and third contacts) of all electrodes of the lead 410 would be electrically coupled creating, at least in one embodiment, two effective conductors extending the length of the lead 410 to connect all of the electrodes (not shown) of the lead 410.

Figure 13A:
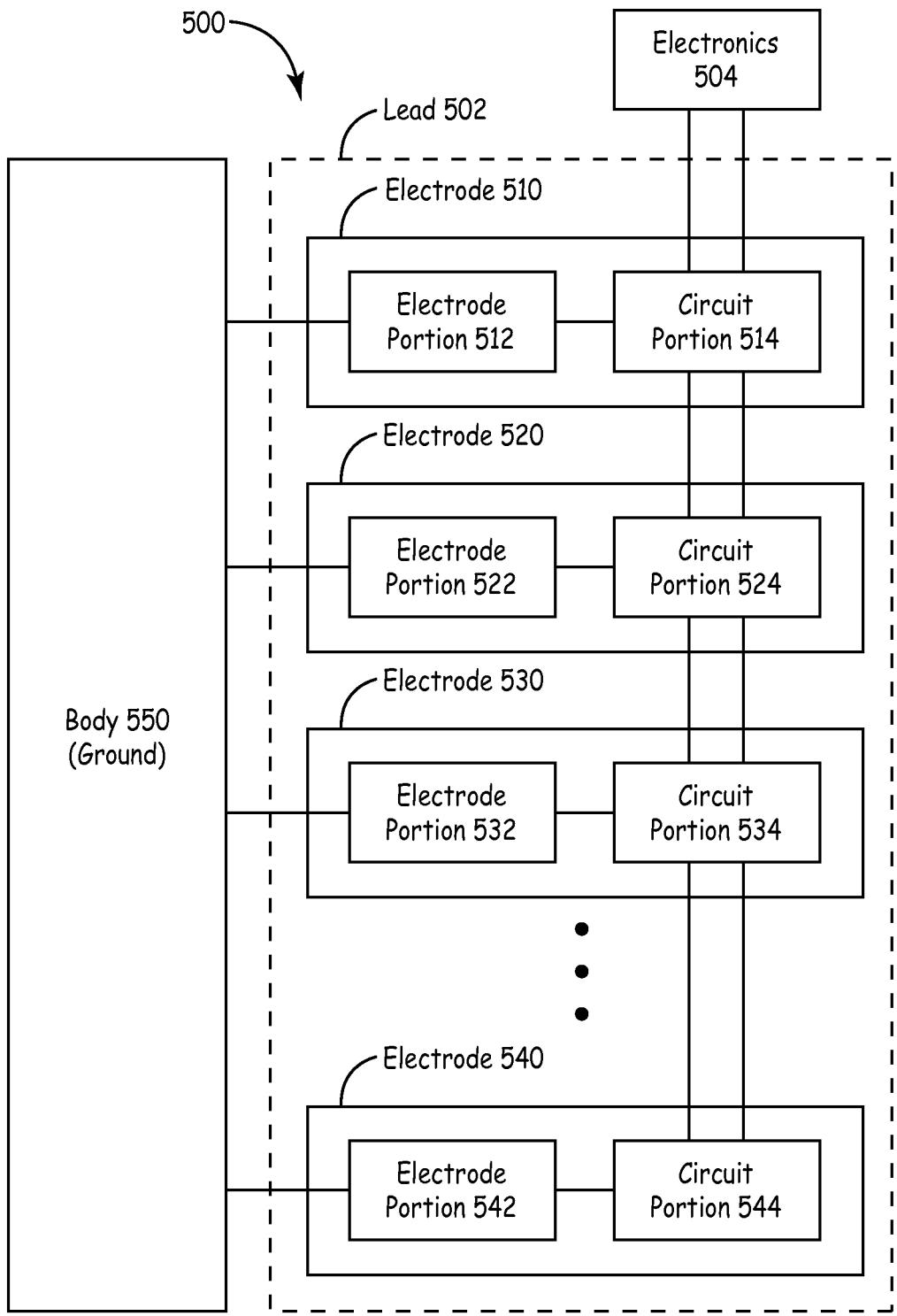
FIG. 13A is a diagrammatic view of an exemplary lead system.
Figure 13B:
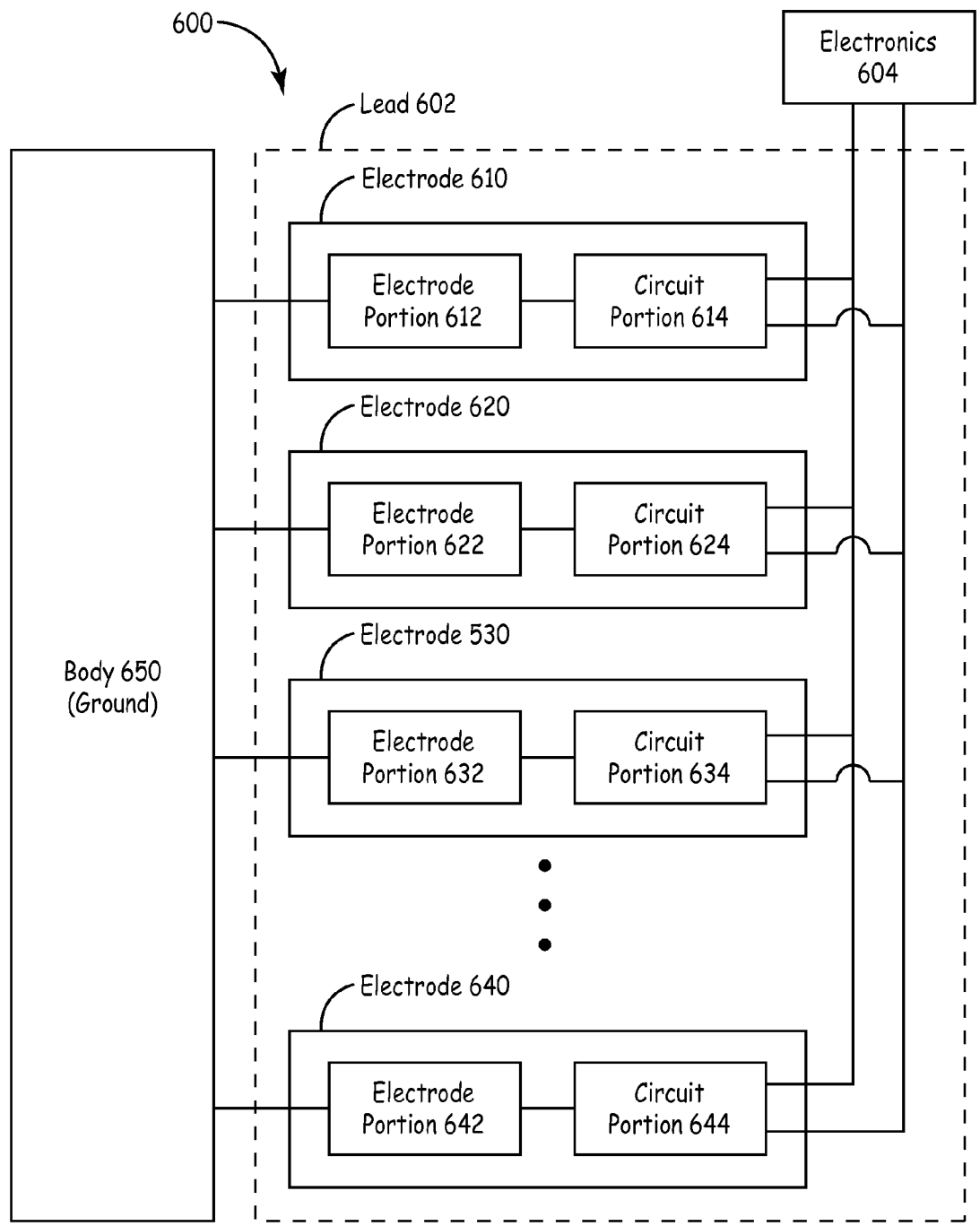
FIG. 13B is a diagrammatic view of another exemplary lead system.

A diagrammatic view of an exemplary lead system having a serial configuration is shown in FIG. 13A and a diagrammatic view of an exemplary lead system having a parallel configuration is shown in FIG. 13B.

Lead system 500 includes a lead 502 and electronics 504 (e.g., of an implantable device). The lead 502 includes one or more electrodes 510, 520, 530, 540 (e.g., functionally intelligent electrodes). Each electrode 510, 520, 530, 540 includes an electrode portion 512, 522, 532, 542 and a circuit portion 514, 524, 534, 544, respectively. When the lead 502 is located in contact with body 550, the electrode portion 512, 522, 532, 542 of the one or more electrodes 510, 520, 530, 540 is electrically coupled to the body 550 (e.g., the ground of the circuit) as shown by the lines extending between each electrode portion 512, 522, 532, 542 and the body 550.

The electronics 504 are electrically coupled to each circuit portion 514, 524, 534, 544 of the electrodes 510, 520, 530, 540 in series. In other words, each circuit portion 514, 524, 534, 544 includes two incoming connections and two outgoing connections. Within each electrode 510, 520, 530, 540, each of the incoming connections is electrically coupled to one of the outgoing connections to form a pass-through connection (e.g., similar to the contacts 260, 262, 264, 266 of the circuit portion 240 of the electrode 200 as described herein). The outgoing connections of each electrode, e.g., electrode 520, are electrically coupled (with a coil conductor, cable conductor, etc.) to the incoming connections of the next electrode, e.g., electrode 530, to connect all of the electrodes 510, 520, 530, 540 in series.

As such, in this configuration, the circuit portion 514, 524, 534, 544 may include four contacts or connections. Further, a line extends between each of the circuit portions 514, 524, 534, 544 and the respective electrode portions 512, 522, 532, 542 representing an electrical coupling.

Lead system 600 includes a lead 602 and electronics 604. The lead 602 includes one or more electrodes 610, 620, 630, 640. Each electrode 610, 620, 630, 640 includes an electrode portion 612, 622, 632, 642 and a circuit portion 614, 624, 634, 644, respectively. When the lead 602 is located in contact with body 650 (e.g., the ground of the circuit), the electrode portion 612, 622, 632, 642 of the one or more electrodes 610, 620, 630, 640 is electrically coupled to the body 650 as shown by the lines extending between each electrode portion 612, 622, 632, 642 and the body 650.

The electronics 604 are electrically coupled to each circuit portion 614, 624, 634, 644 of the electrodes 610, 620, 630, 640 in parallel. In other words, each circuit portion 614, 624, 634, 644 includes two incoming connections that are each electrically coupled to the same two conductors extending through the lead 602. As such, in this configuration, the circuit portion 614, 624, 634, 644 may include two contacts or connections. Further, a line extends between each of the circuit portions 614, 624, 634, 644 and the respective electrode portions 612, 622, 632, 642 representing an electrical coupling.

The cylindrical electrode portions and circuit portions of the exemplary electrodes described herein may be coupled in various ways. For example, the circuit portions may include a coupling structure to be coupled (e.g., laser welded, adhered, etc.) to the cylindrical electrode portion. Further, for example, the cylindrical electrode portions may include apertures and/or structures that correspond to and couple with the coupling structure of the circuit portion. Exemplary electrodes having coupling structures are described herein with reference to FIGS. 14-16 (e.g., an exemplary electrode 700 including circuit portion including a coupling structure that is a flange) and FIGS. 17-20 (e.g., an exemplary electrode 800 including circuit portion including a coupling structure that is a tongue and a cylindrical electrode portion including a corresponding structure that is an aperture).

Figure 14:
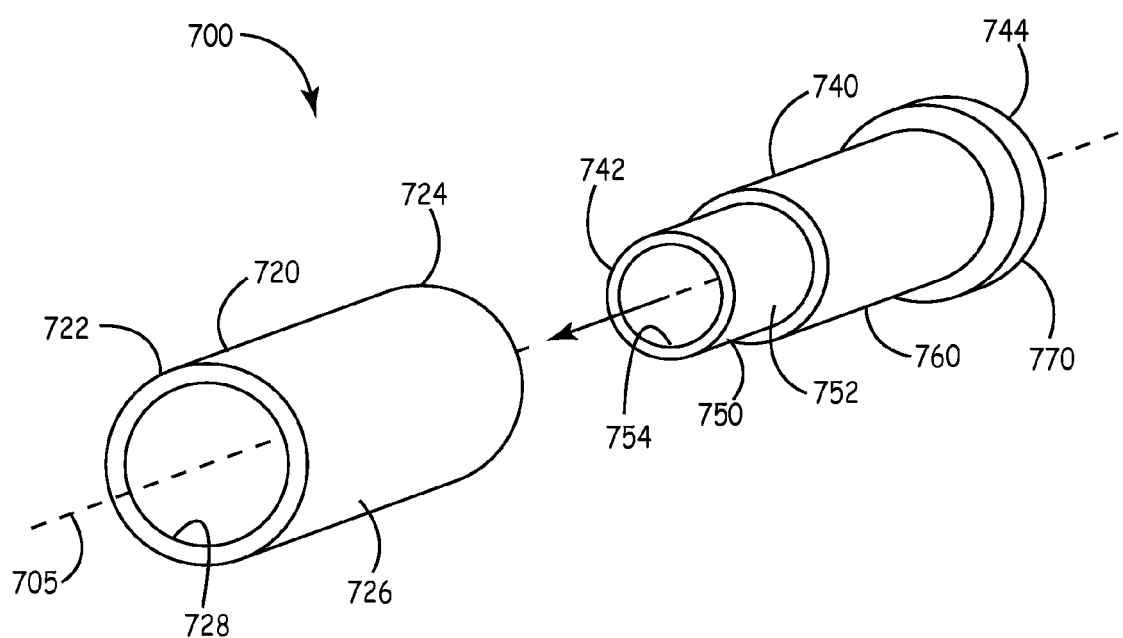
FIG. 14 is an exploded, perspective view of another exemplary electrode.
Figure 15:
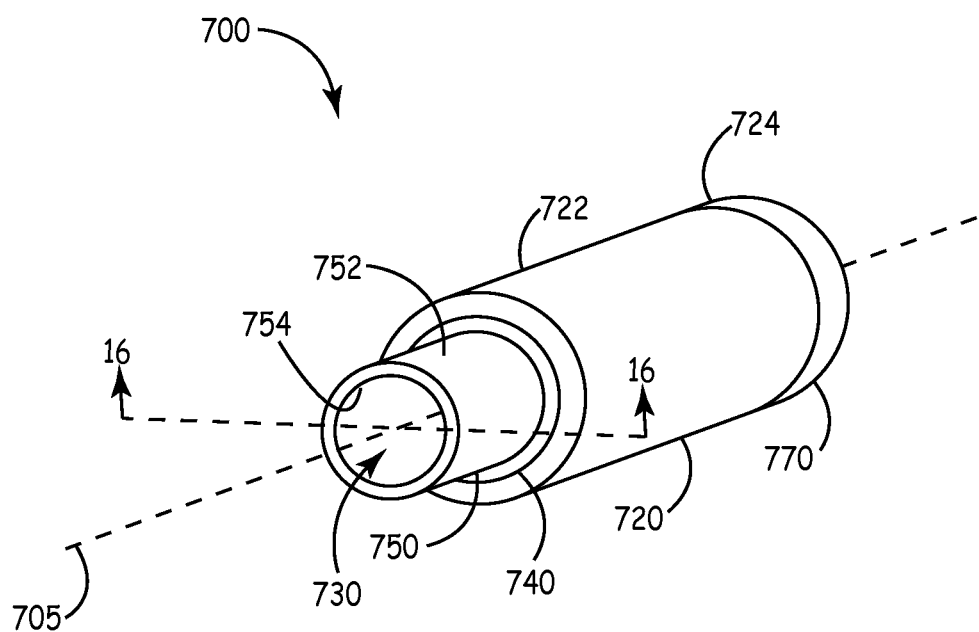
FIG. 15 is a perspective view of the electrode of FIG. 14.
Figure 16:
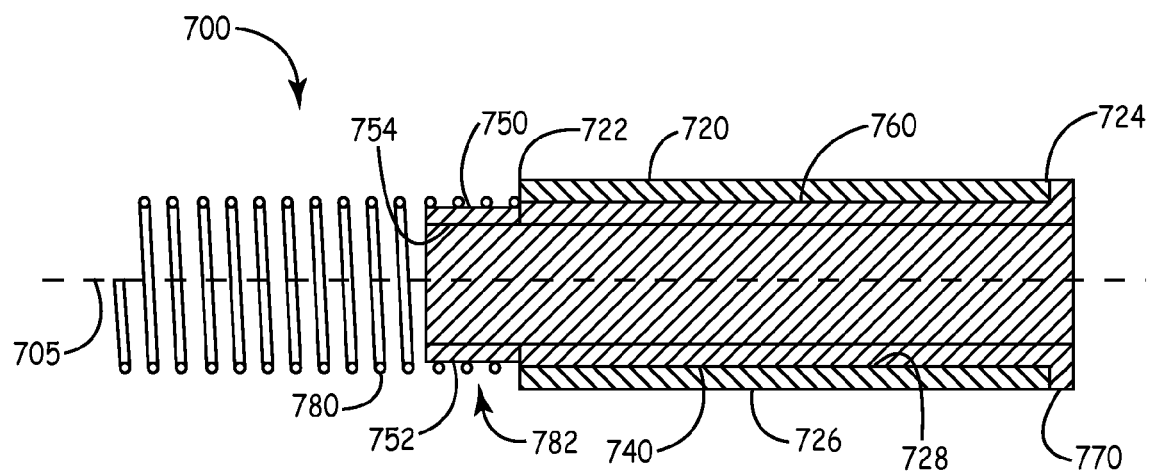
FIG. 16 is a cross-sectional view of the electrode of FIG. 15 taken along line 16-16 and further including a coil conductor.
Figure 17:
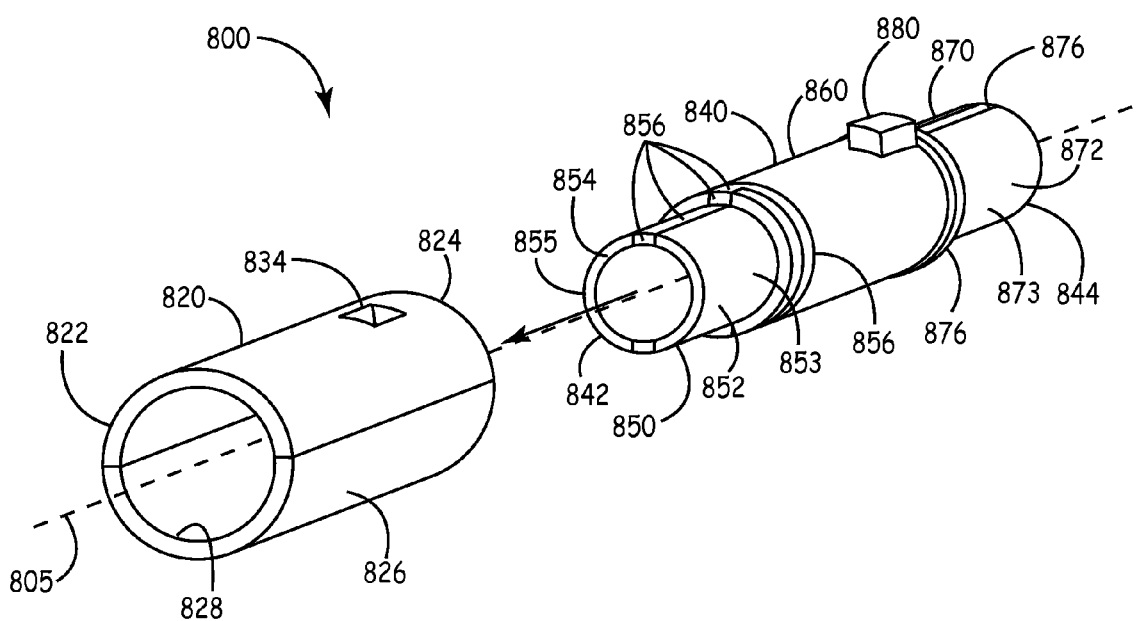
FIG. 17 is an exploded, perspective view of another exemplary electrode.

FIGS. 14-16 depict another exemplary electrode 700. The electrode 700 includes a cylindrical electrode portion 720 and a circuit portion 740. The cylindrical electrode portion 720 extends along an axis 705 from a proximal end 722 to a distal end 724 and includes a body-contacting outer surface 726 and an inner surface 728.

The circuit portion 740 extends along the axis 705 from a proximal end 742 to a distal end 744. Further, the circuit portion 740 includes a contact portion 750 located proximate the proximal end 742, a flange portion 770 located proximate the distal end 744, and a central portion 760 located between the contact portion 750 and the flange portion 770. Although not depicted, contacts, e.g., such as the first and second contacts 260, 262 of the electrode 200 as described herein with reference to FIG. 5, may be located on the outer surface 752 or inner surface 754 of the contact portion 750 and may present arcuate contact surfaces facing in a direction towards axis 705 or facing in a direction away from axis 705. Further, although not depicted, the circuit portion 740 may include integrated circuits, connectors, and isolation substrates such as described herein. For example, the central portion 760 may include an integrated circuit electrically coupled to contacts located on the contact portion 750 and isolated from the cylindrical electrode portion 720 by an isolation substrate.

The circuit portion 740 may be combined with the cylindrical electrode portion 720 to form electrode 700 (see FIG. 15) such that it appears to be a conventional electrode. For example, the circuit portion 740 extends along and conforms to at least a portion of the inner surface 728 of the cylindrical electrode portion 720 (e.g., between at least the proximal end 722 and the distal end 724). Further, the circuit portion 740 defines at least a portion of an opening 730 extending along the axis 705 from the proximal end 722 to the distal end 724 of the cylindrical electrode portion 720. Still further, the contact portion 750 of the circuit portion 740 may include contacts that present arcuate contact surfaces (e.g., arcuate contact surfaces on the outer surface 752 facing in a direction away from the axis 705 or on the inner surface 754 facing in a direction towards the axis 705).

When the electrode 700 is assembled (see FIG. 15), the contact portion 750 extends past the proximal end 722 of the cylindrical electrode portion 720 such that, e.g., a coil conductor may be electrically coupled to contacts located on the contact portion 750 (see FIG. 16). A coil conductor 780 is depicted in FIG. 16 and is electrically coupled to the outer surface 752 of the contact portion 750 of the circuit portion 740 proximate location 782. The coil conductor 780 may be welded (e.g., laser welded), crimped, and/or staked to the contact portion 750. Although not shown, the contact portion 750 may be encapsulated, enclosed, and/or insulated by a portion of the elongated body of a lead (e.g., elongated body 60 of lead 50 as shown in FIGS. 2-3).

Further, when the electrode 700 is assembled, the flange portion 770 is mechanically coupled to the distal end 724 of the cylindrical electrode portion 720. In one or more embodiments, the flange portion 770 is welded to the distal end 724 of the cylindrical electrode portion 720. Further, in one or more embodiments, at least a portion of the flange portion 770 includes conductive material to electrically couple an integrated circuit of the circuit portion 740 and the cylindrical electrode portion 720. Still further, although the flange portion 770 as depicted extends around the entire circumference of the circuit portion 740, in one or more embodiments, the flange portion 770 may extend only partially around the circumference of the circuit portion 740 and/or may include one or more portions, each of which may extend partially around the circumference of the circuit portion 740.

FIGS. 17-20 depict another exemplary electrode 800. The electrode 800 includes a cylindrical electrode portion 820 and a circuit portion 840. The cylindrical electrode portion 820 extends along an axis 805 from a proximal end 822 to a distal end 824 and includes a body-contacting outer surface 826 and an inner surface 828. Further, the cylindrical electrode portion 820 includes two halves that may be, e.g., sandwiched around the circuit portion 840 when assembled.

The cylindrical electrode portion 820 further includes an aperture 834 for receiving a tongue portion 880 of the circuit portion 840. As depicted, the aperture 834 is defined, or extends, from the inner surface 828 to the outer surface 826. In one or more embodiments, the aperture 834 may only partially extend from the inner surface 828 through the cylindrical electrode portion 820.

The circuit portion 840 extends along the axis 805 from a proximal end 842 to a distal end 844. Further, the circuit portion 840 includes a first contact portion 850 located proximate the proximal end 842 (e.g., at least partially located beyond the proximal end 822 of the cylindrical electrode portion 820 when the electrode 800 is assembled), a second contact portion 870 located proximate the distal end 844 (e.g., at least partially located beyond the distal end 824 of the cylindrical electrode portion 820 when the electrode 800 is assembled), and a central portion 860 located between the first contact portion 850 and the second contact portion 870. Still further, the circuit portion 840 includes the tongue portion 880 extending outwardly from the central portion 860. When the cylindrical electrode portion 820 and the circuit portion 840 are assembled together to form the electrode 800 (see FIGS. 18-19), the tongue portion 880 is received by the aperture 834 of the cylindrical electrode portion 820.

Each of the first and the second contact portions 850, 870 includes two contacts and insulation material. The first contact portion 850 includes first contact 852, second contact 854, and insulation material 856. The second contact portion 870 includes third contact 872, fourth contact 874, and insulation material 876. The insulation material 856, 876 electrically isolates the contacts 852, 854, 872, 874 from each other as well as the central portion 860. Further, the contacts 852, 854, 872, 874 include arcuate contacts surfaces 853, 855, 873, 875, respectively, facing in a direction away from axis 805 (in other words, outwardly from axis 805) for electrical coupling to a conductor, e.g., a coil conductor. Although not shown, the contacts 852, 854, 872, 874 are electrically isolated from the cylindrical electrode portion 820 with, e.g., additional insulation material position proximate location 869. Further, although not shown, the contact portions 850, 870 may be encapsulated, enclosed, and/or insulated by a portion of the elongated body of a lead (e.g., elongated body 60 of lead 50 as shown in FIGS. 2-3). Still further, similar to the contacts 260, 262, 264, 266 described herein with reference to FIGS. 5-10, the first contact 852 may be electrically coupled to the third contact 872 and the second contact 854 may be electrically coupled to the fourth contact 874.

Figure 19:
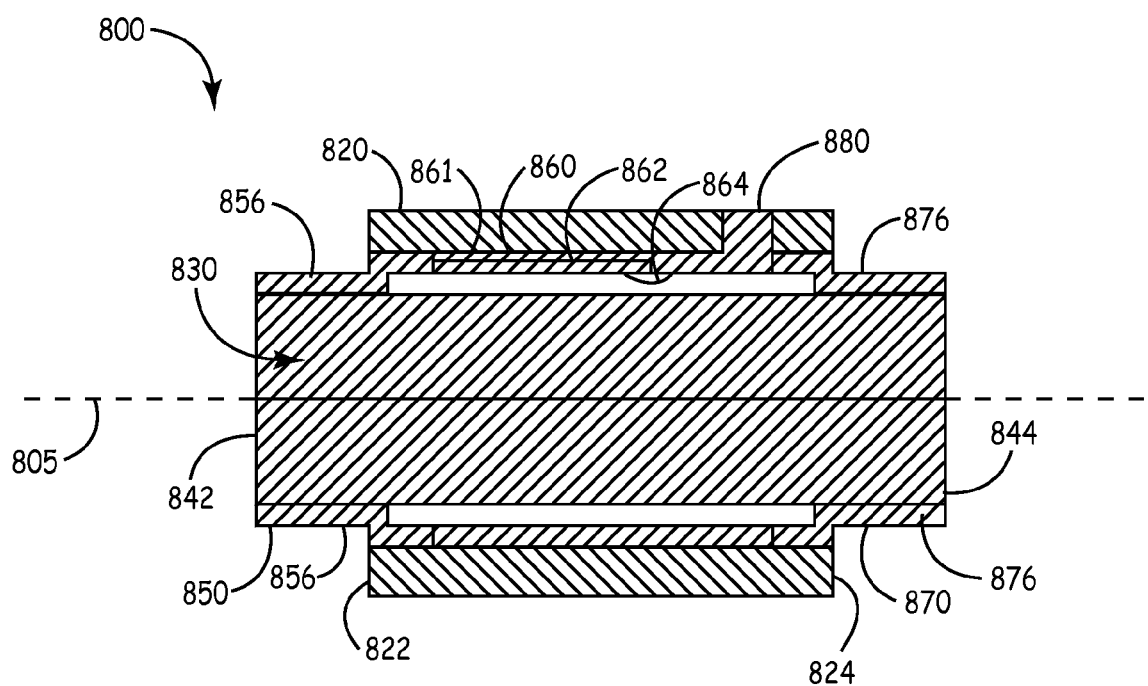
FIG. 19 is a cross-sectional view of the electrode of FIG. 18 taken along line 19-19.

The central portion 860 includes an integrated circuit 862 and an isolation substrate 861 (see FIG. 19). The isolation substrate 861 electrically isolates the integrated circuit 862 from the cylindrical electrode portion 820. Further, the integrated circuit 862 is electrically coupled to each of the contacts 852, 854 and the cylindrical electrode portion 820 (e.g., with use of a backside connection). For example, the integrated circuit 862 is electrically coupled to the first contact 852 with connector 866 (see FIG. 20). Further, for example, the integrated circuit 862 is electrically coupled to the cylindrical electrode portion 820 with connector 864, which connects to the tongue portion 880 (see FIG. 19) (e.g., the tongue portion 880 may electrically couple to the cylindrical electrode portion 820 to the integrated circuit 882). Further, the tongue portion 880 may be mechanically coupled (e.g., welded) to electrode portion 820 (see FIG. 19).

Figure 18:
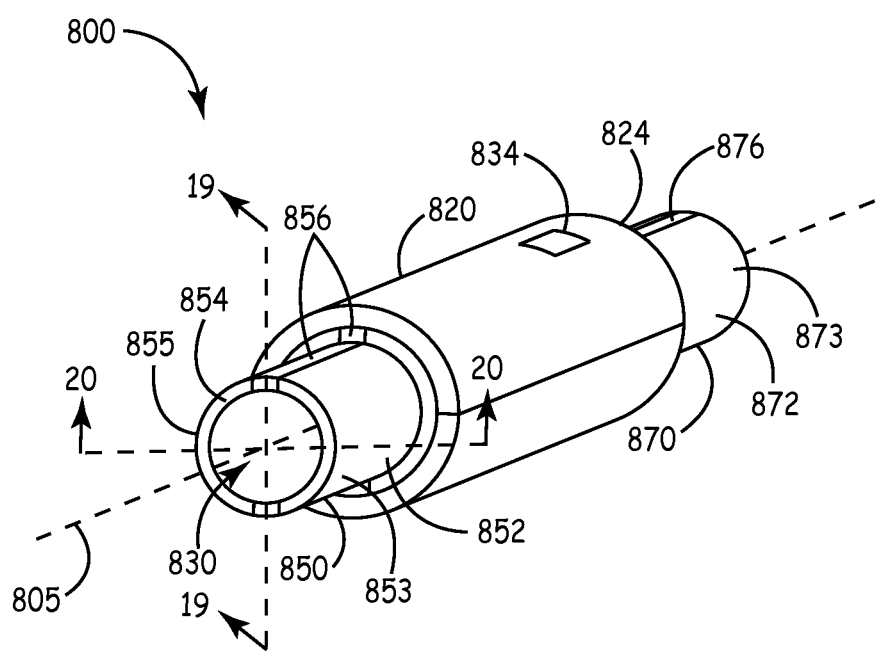
FIG. 18 is a perspective view of the electrode of FIG. 17.
Figure 20:
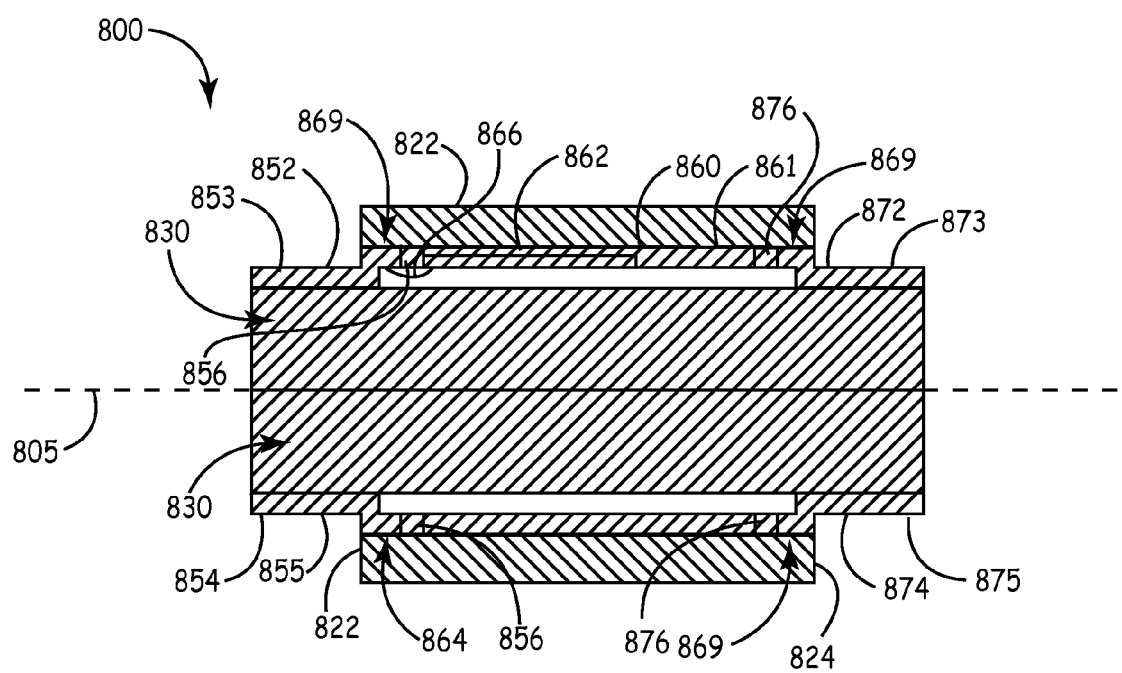
FIG. 20 is a cross-sectional view of the electrode of FIG. 18 taken along line 20-20.

The circuit portion 840 is combined with the cylindrical electrode portion 820 to form electrode 800 (see FIGS. 18-20)

such that it appears to be a conventional electrode. For example, the circuit portion 840 extends along and conforms to at least a portion of the inner surface 828 of the cylindrical electrode portion 820 (e.g., at least between the proximal end 822 and the distal end 824). Further, the circuit portion 840 defines at least a portion of an opening 830 extending along the axis 805 from the proximal end 822 to the distal end 824 of the cylindrical electrode portion 820. Still further, the contacts 852, 854, 872, 874 include arcuate contact surfaces 853, 855, 873, 875, respectively, facing in a direction away from the axis 805. In one or more embodiments, the contacts 852, 854, 872, 874 may include arcuate contact surfaces facing in a direction towards the axis 805. Further, the contacts 852, 854 may be at least partially located beyond the proximal end 822 of the cylindrical electrode portion 820 and the contacts 872, 874 may be at least partially located beyond the distal end 824 of the cylindrical electrode portion 820.

Figure 21:
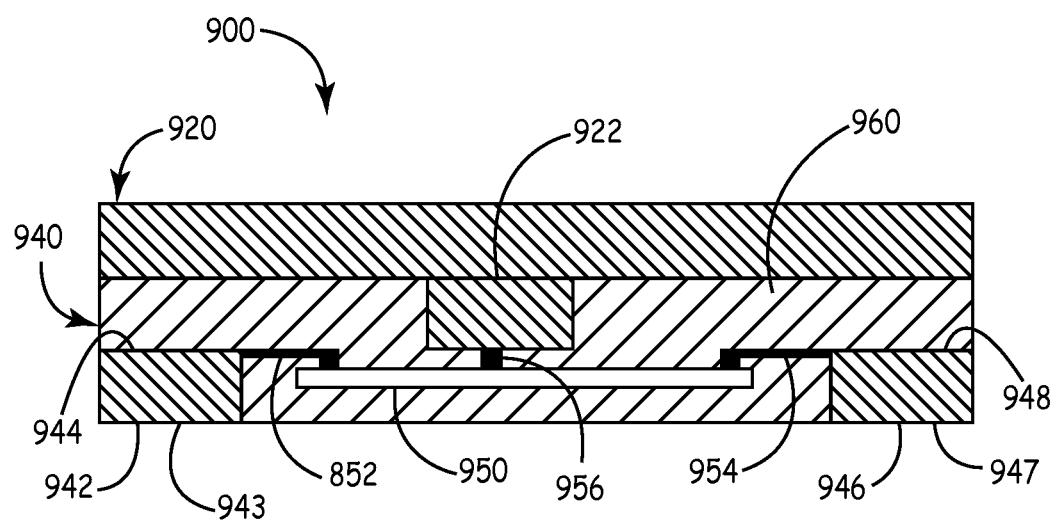
FIG. 21 is a cross-sectional view of a portion of an exemplary electrode.

A cross-sectional schematic view of a portion of an exemplary electrode 900 is shown in FIG. 21. The electrode 900 includes a cylindrical electrode portion 920 and a circuit portion 940. In this embodiment, the cylindrical electrode portion 920 includes a contact portion 922 extending inwardly towards the circuit portion 940. In one or more embodiments, the contact portion 922 is integral with the cylindrical electrode portion 920 and/or formed of the same material as the cylindrical electrode portion 920.

The circuit portion 940 includes a first contact 942, a second contact 946, an integrated circuit 950, and isolation substrate 960 electrically isolating the first contact 942, the second contact 946, the integrated circuit 950, the cylindrical electrode portion 920, etc. The first contact 942 and second contact 946 include inner contact surfaces 943, 947 and outer contact surfaces 944, 948, respectively. Although not shown, a conductor, e.g., a cable or coil conductor, may be electrically coupled to either inner or outer contact surfaces 943, 944, 947, 948 of the contacts 942, 946. Further, although not apparent from the partial, cross-sectional view of FIG. 21, the inner and outer contacts surfaces 943, 944, 947, 948 may be arcuate contact surfaces similar to the other arcuate contact surfaces described herein.

The integrated circuit 950 may be substantially similar to the other integrated circuits described herein, e.g., integrated circuit 270 of the electrode 200 as described herein with references to FIGS. 5-10. Further, the integrated circuit 950 is electrically coupled to the first contact 942 by a first connector 952 (e.g., a cable conductor), to the second contact 946 by a second connector 954 (e.g., a cable conductor), and to the contact portion 922 by a third connector 956 (e.g., a solder bump or interconnect conductor).

Although the cross section of FIG. 21 only depicts a portion of the electrode 900, one or more (e.g., all) of the components shown therein may extend around the entire electrode 900 (e.g., the electrode portion 920 may extend around the entire electrode 900, etc.). Further, any portion of the circuit portion 940 (e.g., the integrated circuit 950 and/or the isolation substrate 960) may be flex-tape circuit or molded interconnects technology. In one or more embodiments, the integrated circuit 950 will flex, e.g., to allow small electrode diameters.

Figure 22:
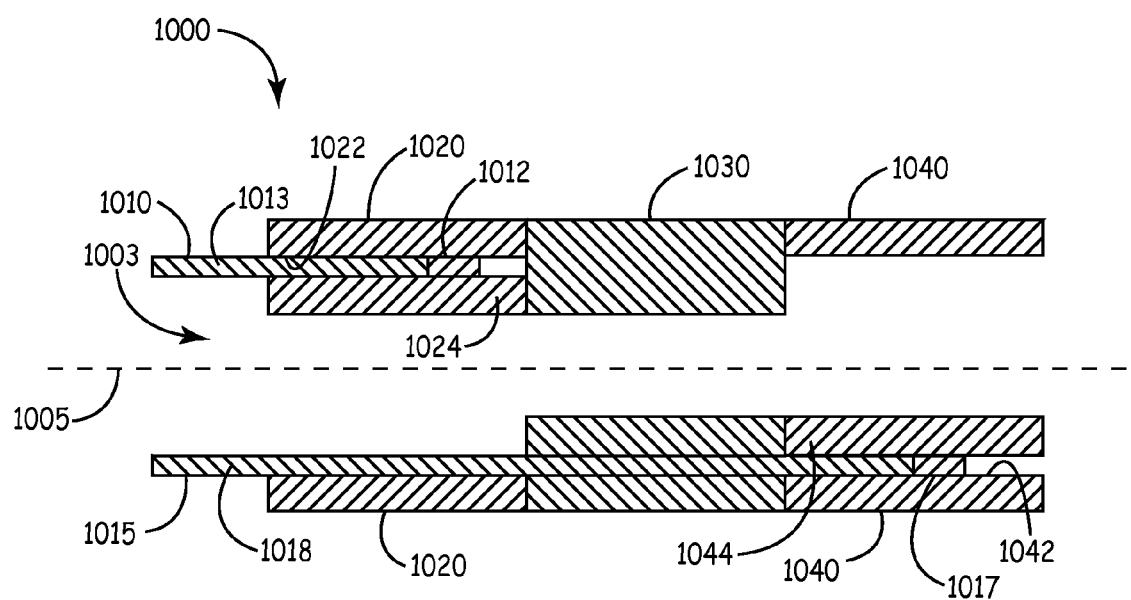
FIG. 22 is a cross-sectional view of a portion of a lead including two conventional ring electrodes and two cable conductors.

A cross-sectional view of a portion of a lead 1000 is depicted in FIG. 22. The lead 1000 includes an opening 1003 (e.g., a cylindrical opening) extending along axis 1005 and a first conventional ring electrode 1020, a second conventional ring electrode 1040, and an insulation portion 1030 electrically isolating the first conventional ring electrode 1020 from the second conventional ring electrode 1040. Each of the ring electrodes 1020, 1040 includes inner contact surfaces 1022, 1042, respectively, for electrical coupling to, e.g., a conductor.

Two cable conductors 1010, 1015 extend from a medical device (not shown) through lead 1000. The first cable conductor 1010 terminates proximate the first ring electrode 1020 and the second cable conductor 1015 terminates proximate the second ring electrode 1040. Each of the two cable conductors 1010, 1015 includes conductive material 1012, 1017 and an outer insulative covering 1013, 1018 to electrically insulate the conductive material 1012, 1017. The outer insulative covering 1013, 1018 is stripped from the ends of the cable conductors 1010, 1015 thereby exposing the conductive material 1012, 1017 such that the conductive material 1012, 1017 can be electrically coupled to the ring electrodes 1020, 1040 by contacting the contact surfaces 1022, 1042 of the ring electrodes 1020, 1040.

The lead 1000 further includes a first coupling portion 1024 for electrically coupling the conductive material 1012 of the first cable conductor 1010 to the first conventional ring electrode 1020 and a second coupling portion 1044 for electrically coupling the conductive material 1017 of the second cable conductor 1015 to the second conventional ring electrode 1040. In one or more embodiments, the coupling portions 1024, 1044 are crimped against the ring electrodes 1020, 1040 to secure the conductive material 1012, 1017 of cable conductors 1010, 1015 with contact surfaces 1022, 1042 of the ring electrodes 1020, 1040 to form an electrical coupling thereof.

Figure 23:
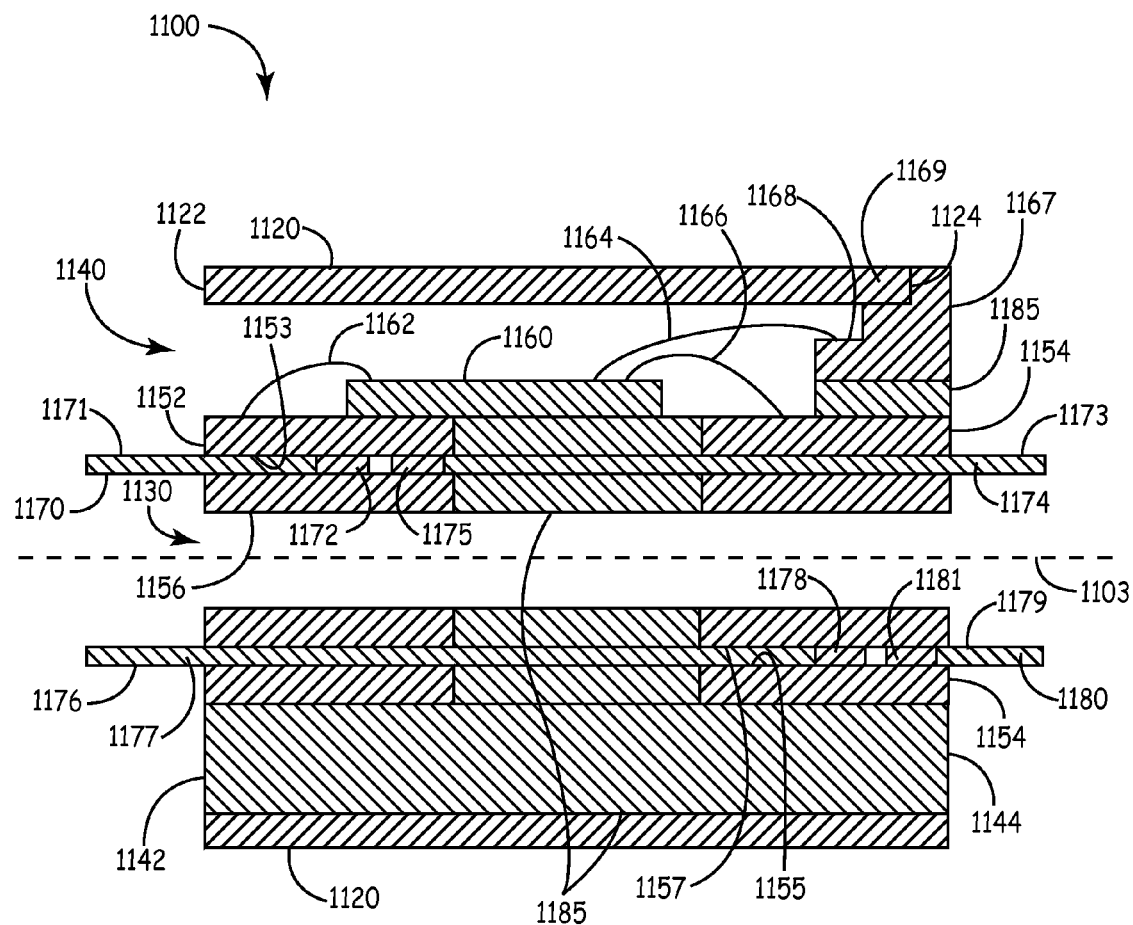
FIG. 23 is a cross-sectional view of another exemplary electrode including two cable conductors.

A cross-sectional view of an exemplary electrode 1100 that resembles a conventional electrode (such as conventional electrodes 1020, 1040 of FIG. 22) is depicted in FIG. 23.

The electrode 1100 includes a cylindrical electrode portion 1120 extending from a first end 1122 to a second end 1124 and a circuit portion 1140 extending from a first end 1142 to a second end 1144. Further, the electrode 1100 extends along axis 1103 and defines an opening 1130 (e.g., a cylindrical opening) therethrough and along axis 1103.

The circuit portion 1140 includes a first contact 1152, a second contact 1154, an integrated circuit 1160, and isolation material 1185. In one or more embodiments, the integrated circuit 1160 is electrically coupled to the first contact 1152 by a connector 1162 (e.g., a wire conductor), to the second contact 1154 by a connector 1166 (e.g., a wire conductor), and to the cylindrical electrode portion 1120 by a connector 1164 (e.g., a wire conductor) contacting a conductive tongue portion 1167 that further contacts the cylindrical electrode portion 1120.

In one or more embodiments, the tongue portion 1167 includes a first step 1168 for contact with the connector 1164 and a second step 1169 for contact with the cylindrical electrode portion 1120. Further, the tongue portion 1167 is electrically isolated from the second contact 1154 by a portion of isolation material 1185.

Although the integrated circuit 1160 is shown adjacent a portion of the first contact 1152, the integrated circuit 1160 is electrically isolated from the first contact 1152 with, e.g., an isolation layer or the substrate of the integrated circuit 1160 itself.

Four cable conductors 1170, 1173, 1176, 1179 extend through a portion of the electrode 1100. Each of the cable conductors 1170, 1173, 1176, 1179 includes conductive material 1172, 1175, 1178, 1181, respectively, and an outer insulative covering 1171, 1174, 1177, 1180, also respectively, to electrically insulate the conductive material 1172, 1175, 1178, 1181. The outer insulative covering 1171, 1174, 1177, 1180 is stripped from the ends of the cable conductors 1170, 1173, 1176, 1179 thereby exposing the conductive material 1172, 1175, 1178, 1181 such that the conductive material 1172, 1175, 1178, 1181 can be electrically coupled to the contacts 1152, 1154 by contacting the contact surfaces 1153, 1155 of the contacts 1152, 1154.

The lead 1100 further includes a first coupling portion 1156 and a second coupling portion 1157. The first coupling portion 1156 electrically couples the conductive material 1172 of the first cable conductor 1170 and the conductive material 1175 of the second cable conductor 1173 to the first contact 1152 (by contacting the contact surface 1153). Further, the second coupling portion 1157 electrically couples the conductive material 1178 of the third cable conductor 1176 and the conductive material 1181 of the fourth cable conductor 1179 to the second contact 1154 (by contacting the contact surface 1155). In one or more embodiments, the coupling portions 1156, 1157 are crimped against the contacts 1152, 1154 to secure the electrical coupling between the conductive material 1172, 1175, 1178, 1181 of the cable conductors 1170, 1173, 1176, 1179 with contact surfaces 1153, 1155 of the contacts 1152, 1154. Although in this embodiment, two cable conductors, e.g., cable conductors 1170, 1173, are shown being coupled together by a coupling portion, e.g., the first coupling portion 1156, in one or more embodiments, a single conductor may be utilized that has insulative covering removed at locations along its length that correspond to the coupling portions of the electrodes that are electrically coupled to contact 1152.

In the lead 1000 as shown in the FIG. 22, each conventional ring electrode 1020, 1040 required a separate cable conductor. In contrast, a lead having multiple electrodes 1100 as shown in FIG. 23 may only require two conductors (or multiple conductors coupled together, e.g., first cable conductor 1170 and second cable conductor 1173, to effectively form two singular cable conductors) extending through the lead to couple the multiple electrodes to circuit of device 10 because each electrode can share the same two conductors.

Figure 24:
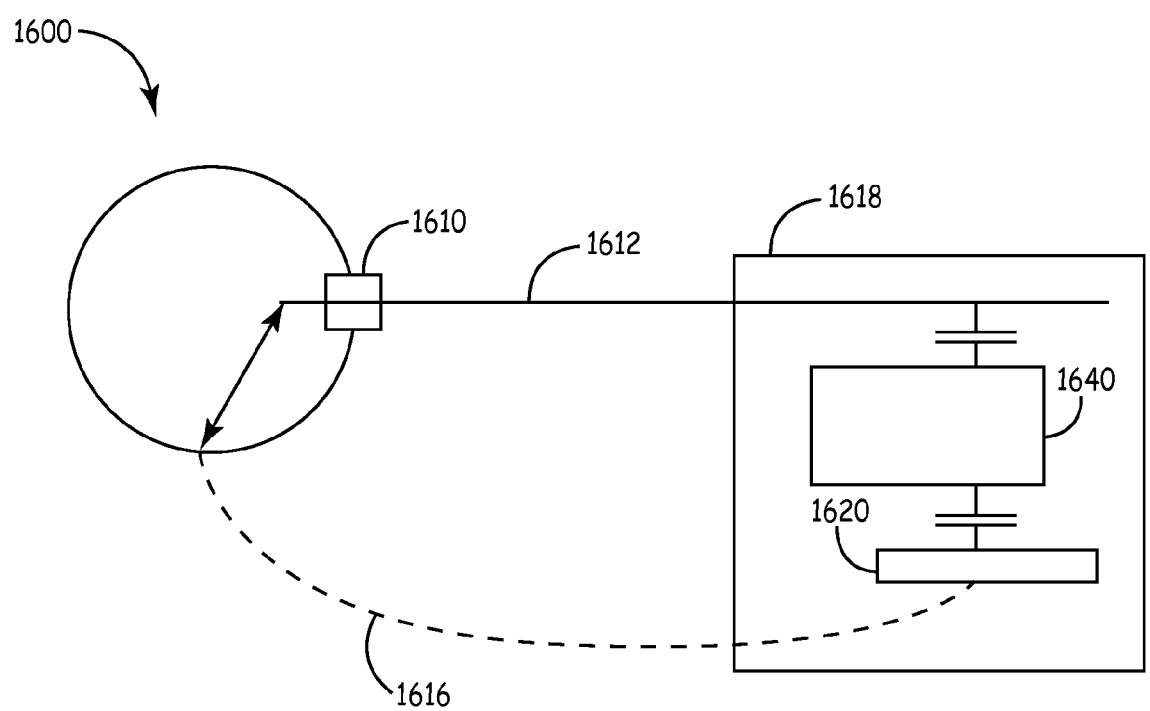
FIG. 24 is a diagrammatic view of a lead system including an exemplary electrode utilizing capacitive coupling.

The electrodes described herein may utilize capacitive coupling without the use of connectors or direct physical contact between the circuit portions, electrode portions, and conductors. A diagrammatic view of an exemplary system 1600 including an electrode 1618 utilizing capacitive couplings is depicted in FIG. 24.

The system 1600 includes an electronic device 1610, e.g., a pulse generator, capacitively coupled to electrode 1618. A conductor 1612 extends from the device 1610 to a location proximate the electrode 1618. The electrode 1618 includes an integrated circuit 1640 capacitively coupleable to the conductor 1612 (as represented by the capacitor located between the integrated circuit 1640 and the conductor 1612) and an electrode portion 1620 capacitively coupleable to the integrated circuit 1640 (as represented by the capacitor located between the integrated circuit 1640 and the electrode portion 1620).

Although the integrated circuit 1640 is described as being capacitively coupled to the conductor 1612 and the electrode portion 1620, the integrated circuit 1640 itself may be electromagnetically shielded from any parasitic signals, e.g., by use of a dielectric layer (e.g., an oxide layer) and/or a metal layer. To obtain the capacitive coupling, metal contacts (e.g., capacitive plates) electrically coupled to the integrated circuit 1640 may extend beyond the electromagnetic shielding of the integrated circuit 1640 to be capacitively coupled to both the conductor 1612 and the electrode portion 1620. For example, the backplane of the integrated circuit 1640 can be adhered to the electrode portion 1620 and the other side of the integrated circuit 1640 may have contacts located at a specific spot outside of the electromagnetic shielding for capacitive coupling to, e.g., either the conductor 1612 or the electrode portion 1620, while all other circuitry (e.g., on the integrated circuit 1640) is isolated with a thick oxide layer.

In one or more embodiments, the device 1610 generates a voltage between the conductor 1612 and a contact (not shown) of the integrated circuit 1640. In pacing mode, this voltage is a pacing pulse and if the state of the integrated circuit 1640 allows pacing to occur, the integrated circuit 1640 will capacitively couple with the electrode portion 1620 to deliver the pacing pulse 1614 thereby completing the circuit (shown by the dotted line 1616). In programming mode, the voltage is interpreted as data to set the state of the integrated circuit 1640, e.g., to place the electrode 1618 in the stimulation path.

Although the system 1600 includes a single conductor 1612, the system 1600 may include two or more conductors capacitively coupled to the integrated circuit 1640, e.g., depending on the functionality of the electrode 1618. For example, a lead system may include a lead have multiple switchable electrodes and the integrated circuit of each switchable electrode may be capacitively coupled to two or more conductors extending through the lead.

Figure 25:
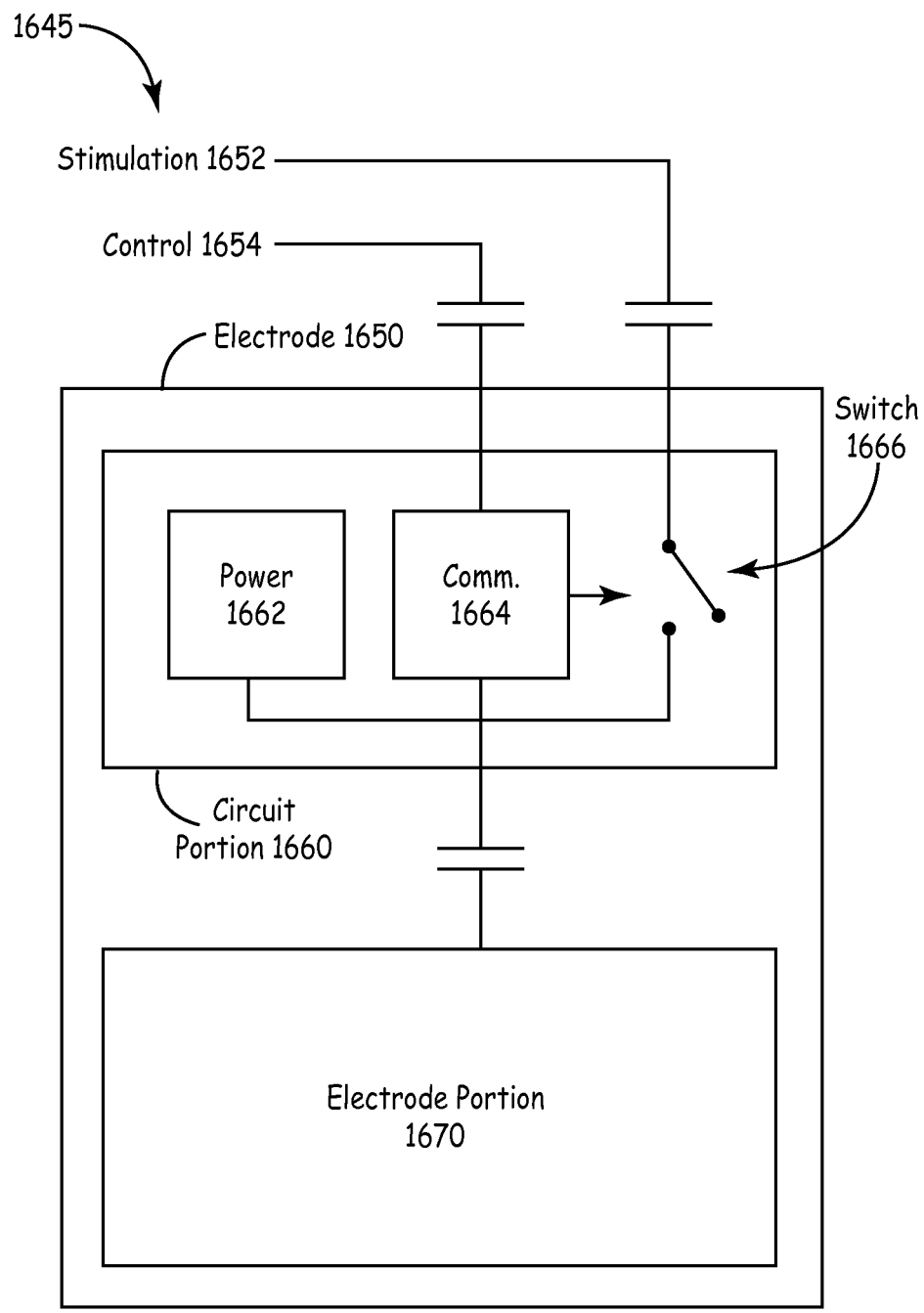
FIG. 25 is a diagrammatic view of a portion of a lead system including an exemplary switchable electrode utilizing capacitive coupling.

One example of a lead system 1645 including an exemplary switchable electrode 1650 utilizing capacitive coupling is depicted in FIG. 25. The switchable electrode 1650 includes a circuit portion 1660 and an electrode portion 1670. The circuit portion 1660 includes communication circuitry 1664, power source 1662 (e.g., for providing power to the communication circuitry 1664, for providing power for stimulation to the electrode portion 1670, etc.), and a switch 1666.

The system provides a stimulation signal 1652 and a control signal 1654, e.g., from a device, transmitted over a medium, e.g., a conductor. The control signal 1654 is capacitively coupled to communication circuitry 1664 of the circuit portion 1660 (as represented by the capacitor located between the communication circuitry 1664 and the control signal 1654) and the stimulation signal 1652 is capacitively coupled to the switch 1666 (as represented by the capacitor located between the switch 1666 and the stimulation signal 1652). The electrode 1650 may be configured such that communication circuitry 1664 may open or close the switch depending on the control signal 1654 delivered to the communication circuitry 1664. When the switch is closed, the stimulation signal 1652 may be transmitted to the electrode portion 1670 (e.g., contacting a body portion to transmit the stimulation signal 1652 therein) through another capacitive coupling (as represented by the capacitor located between the circuit portion 1660 and the electrode portion 1670).

Further, although not shown, the power source 1662 may also be capacitively coupled to a conductor (e.g., a power supply conductor). In one or more embodiments, the power source 1662 may be self-contained (e.g., a battery). Still further, although not shown, the power source 1662 may also be capacitively coupled to the control signal 1654 using the same capacitance drawn between the communication circuitry 1664 and the control signal 1654. In other words, both power and control signals could be provided through the same conductor. In such an embodiment, the circuit portion 1660 would know what to interpret as communication based on a communication protocol.

Figure 26:
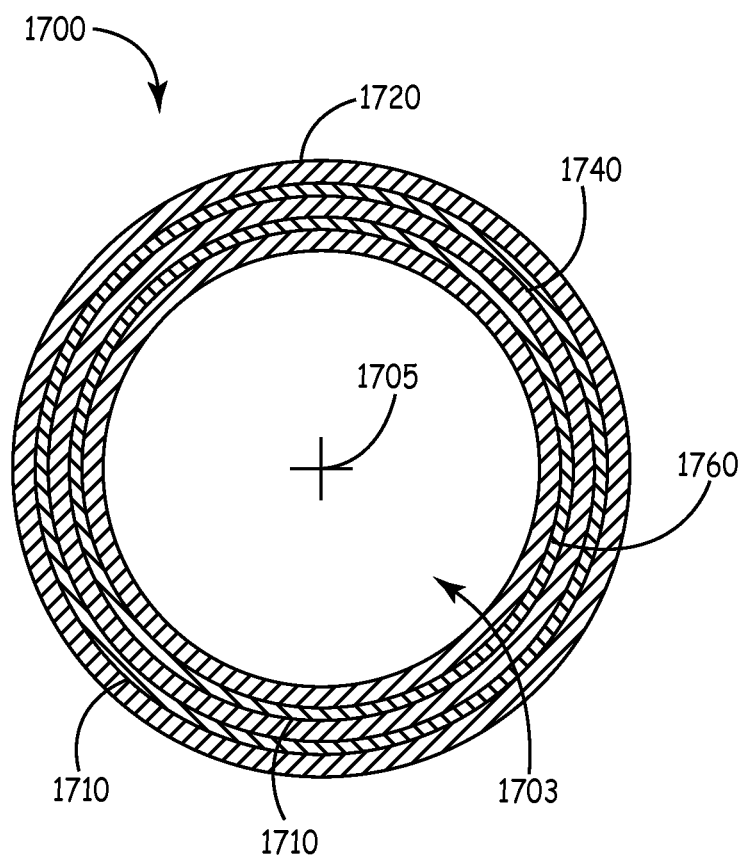
FIG. 26 is a cross-sectional view of an exemplary electrode utilizing capacitive coupling.

A cross-sectional view of an exemplary electrode 1700 utilizing capacitive coupling is depicted in FIG. 26. The electrode 1700 extends along axis 1705 and at least partially defines an opening 1703 along axis 1705. The electrode 1700 includes an electrode portion 1720, a circuit portion 1740, and a conductor portion 1760 with each portion being electrically isolated from each other by a dielectric layer 1710, e.g., an oxide layer.

In one or more embodiments, the conductor portion 1760 extends along the length of a lead that includes the electrode 1700. Further, in one or more embodiments, the conductor 1760 includes contact surfaces for contacting a conductor (e.g., a coil conductor). Further, although the embodiment of the electrode 1700 depicted in FIG. 26 includes a single conductor portion 1760, other embodiments may include two more conductor portions 1760 that may extend along the length of the lead or a portion of the lead.

The circuit portion 1740 includes circuitry such that it may be capacitively coupled to the conductor portion 1760 (or portions) to, e.g., receive pacing pulses or data transmissions, transmit data to a device electrically coupled to the conductor portion 1760, etc. For example, the data transmissions may include instructions for the circuit portion 1740 (e.g., instructions to deliver the next pacing pulse to the electrode portion 1720). Further, the circuit portion 1740 includes circuitry such that it may be capacitively coupled to the electrode portion 1720 to, e.g., receive signals from the electrode portion 1720, deliver pacing pulses to the electrode portion 1720, etc.

Figure 27:
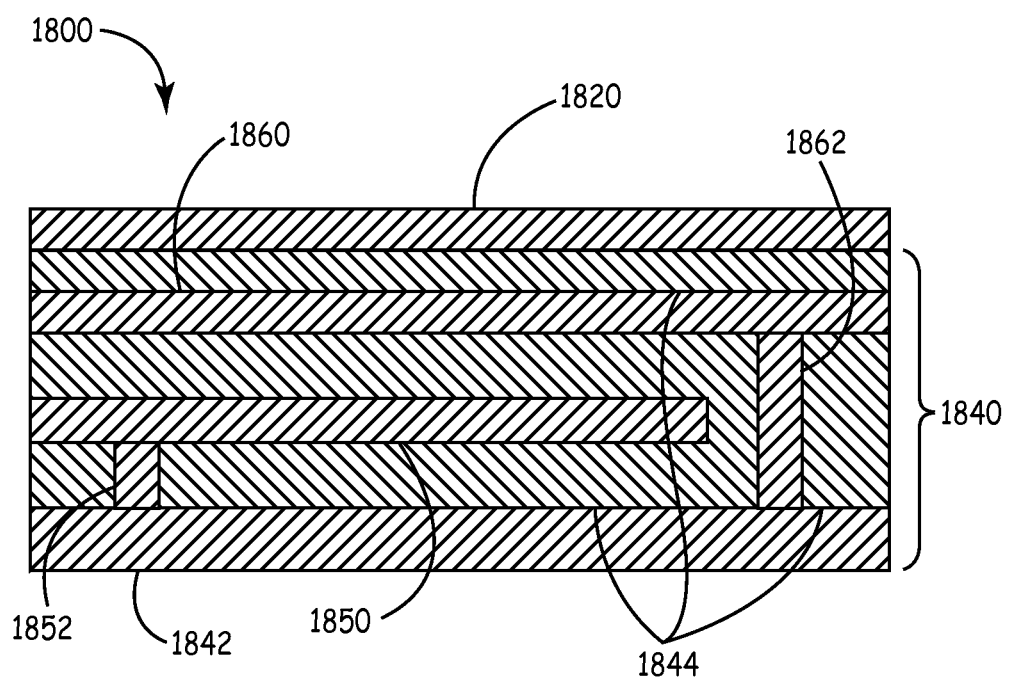
FIG. 27 is a cross-sectional view of a portion of an exemplary electrode utilizing capacitive coupling.

A cross-sectional view of a portion of an exemplary electrode utilizing capacitive coupling is depicted in FIG. 27. The electrode 1800 includes an electrode portion 1820 (for contacting a body portion) and a circuit portion 1840.

The circuit portion includes an integrated circuit device 1842, isolation material 1844, an electromagnetic shield structure 1850, and a capacitive structure 1860.

The electromagnetic shield structure 1850, which is electrically coupled to the integrated circuit 1842 by conductive structure 1852, may shield the integrated circuit device 1842 from parasitic electromagnetic signals. Further, the electromagnetic shield structure 1850 may be formed of any material (e.g., a metal) that is capable of shielding the integrated circuit 1842 from parasitic electromagnetic signals.

The integrated circuit 1842 may be capacitively coupled to the electrode portion 1820 through the use of the capacitive structure 1860 (e.g., a capacitor plate), which is electrically coupled to the integrated circuit 1842 by conductive structure 1862 (e.g., another capacitor plate). The capacitive structure 1860 may be formed of any material (e.g., a metal) that is capable of capacitive coupling with a corresponding structure (e.g., the electrode portion 1820). Further, the capacitive structure 1860 is located beyond the electromagnetic shielding of the shielding structure 1850 so as to, e.g., not be shielded from electromagnetic signals. In one or more embodiments, the capacitive structure 1860 may be positioned such that it is substantially parallel to the corresponding structure (e.g., the electrode portion 1820) to facilitate capacitive coupling therebetween.

Further, the capacitive structure 1860, shield structure 1850, integrated circuit 1842, and electrode portion 1820 are electrically isolated from each other by isolation material 1844 (e.g., a dielectric material). The isolation material 1844, e.g., an oxide, may also assist in the shielding of the integrated circuit 1842, for example, from parasitic electromagnetic signals (e.g., from the capacitive coupling between the capacitive structure 1860 and an electrode portion 1820 and/or from any other parasitic signal generating device or structure).

The circuit portion 1840 (including connections, etc.), similar to the other circuit portions described herein, may be formed using conventional fabrication techniques (e.g., using flexible circuit boards and/or various depositions processes).

Further, although not depicted in FIG. 27, the circuit portion 1840 may include capacitive structures and/or shield structures similar to capacitive structure 1860 and/or shield structure 1850 for capacitive coupling to one or more conductors and/or electrode portions.

Furthermore, a lead including one or more electrodes described herein may be useful when addressing various problems, e.g. lead migration, difficult lead placement, changes in patient condition requiring different lead position, electrode location and anatomical fixation location coupling, etc. Each exemplary electrode and/or lead described herein may be described as having "intelligence." In other words, the leads and/or electrodes include integrated circuitry that is capable of performing some intelligent function, which can be many things. For example, it could be a switching function to select electrodes, perform amplitude modulation, contain pacing circuitry, etc.

Any features, components, and/or properties of any of the embodiments described herein may be incorporated into any other embodiment(s) described herein.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A lead comprising:
   an elongated body; and
   one or more electrodes located along the elongated body, wherein each electrode of the one or more electrodes comprises:
   a cylindrical electrode portion extending along an axis from a proximal end to a distal end and comprising a body-contacting outer surface and an inner surface, wherein the cylindrical electrode portion comprises conductive material, and
   a circuit portion extending along and conforming to at least a portion of the inner surface of the cylindrical electrode portion, wherein the circuit portion further comprises:
   an isolation substrate contacting at least a portion of the inner surface of the cylindrical electrode portion,
   a first contact electrically isolated from the cylindrical electrode portion by the isolation substrate,
   a second contact electrically isolated from the cylindrical electrode portion by the isolation substrate, and
   an integrated circuit electrically coupled to the first contact, the second contact, and the cylindrical electrode portion; and
   wherein the isolation substrate of the circuit portion of the one or more electrodes comprises a flexible substrate.

2. A lead comprising:
   an elongated body; and
   one or more electrodes located along the elongated body, wherein each electrode of the one or more electrodes comprises:
   a cylindrical electrode portion extending along an axis from a proximal end to a distal end and comprising a body-contacting outer surface and an inner surface, wherein the cylindrical electrode portion comprises conductive material, and a circuit portion extending along and conforming to at least a portion of the inner surface of the cylindrical electrode portion, wherein the circuit portion further comprises:

an isolation substrate contacting at least a portion of the inner surface of the cylindrical electrode portion, a first contact electrically isolated from the cylindrical electrode portion by the isolation substrate, a second contact electrically isolated from the cylindrical electrode portion by the isolation substrate, and an integrated circuit electrically coupled to the first contact, the second contact, and the cylindrical electrode portion;

wherein the isolation substrate of the circuit portion of the one or more electrodes comprises a flexible substrate; and wherein the integrated circuit of the circuit portion of the one or more electrodes comprises a flexible integrated circuit.

3. The lead of claim 2, wherein the first contact of the circuit portion of the one or more electrodes is at least partially located beyond the proximal end of the cylindrical electrode portion and the second contact of the circuit portion of the one or more electrodes is at least partially located beyond the proximal end of the cylindrical electrode portion.

4. The lead of claim 2, wherein the circuit portion of the one or more electrodes defines at least a portion of an opening extending along the axis from the distal end to the proximal end of the cylindrical electrode portion.

5. The lead of claim 2, wherein the circuit portion of the one or more electrodes further comprises a coupling structure for use in coupling the cylindrical electrode portion to the circuit portion, wherein the coupling structure of the circuit portion comprises a flange extending away from the axis and coupled to the distal end of the cylindrical electrode portion.

6. The lead of claim 2, wherein the first contact of the circuit portion of the one or more electrodes comprises a first contact surface facing in a direction towards or away from the axis and the second contact of the circuit portion of the one or more electrodes comprises a second contact surface facing in a direction towards or away from the axis.

7. The lead of claim 2, wherein the circuit portion of the one or more electrodes further comprises:

a third contact for electrically coupling to another electrode located distally along the lead, wherein the third contact is electrically isolated from the cylindrical electrode portion by the isolation substrate, wherein the third contact is electrically coupled to the first contact by a conductive trace on the isolation substrate, and a fourth contact for electrically coupling to another electrode located distally along the lead, wherein the fourth contact is electrically isolated from the cylindrical electrode portion by the isolation substrate, wherein the fourth contact is electrically coupled to the second contact by a conductive trace on the isolation substrate.

8. The lead of claim 2, wherein the first and the second contacts of the circuit portion of the one or more electrodes comprise platinum, wherein the first and the second contacts of the circuit portion of the one or more electrodes are formed at least in part from a bulk material.

9. The lead of claim 2, wherein the integrated circuit of the circuit portion of the one or more electrodes comprises a backside contact for electrical connection to the inner surface of the cylindrical electrode portion.

10. The lead of claim 2, wherein the integrated circuit of the circuit portion of the one or more electrodes is capacitively coupled to the cylindrical electrode portion of the one or more electrodes.

11. The lead of claim 2, wherein the lead comprises one or more conductors to electrically couple each of the one or more electrodes, wherein the one or more conductors comprises at least one coil conductor electrically coupled to the first contact of the circuit portion of the one or more electrodes or at least one cable conductor electrically coupled to the second contact of the circuit portion of the one or more electrodes.

12. A lead comprising:

an elongated body; and one or more electrodes located along the elongated body, wherein each electrode of the one or more electrodes comprises:

a cylindrical electrode portion extending along an axis from a proximal end to a distal end and comprising a body-contacting outer surface and an inner surface, wherein the cylindrical electrode portion comprises conductive material, and a circuit portion extending along and conforming to at least a portion of the inner surface of the cylindrical electrode portion, wherein the circuit portion further comprises:

an isolation substrate contacting at least a portion of the inner surface of the cylindrical electrode portion, a first contact electrically isolated from the cylindrical electrode portion by the isolation substrate, a second contact electrically isolated from the cylindrical electrode portion by the isolation substrate, and an integrated circuit electrically coupled to the first contact, the second contact, and the cylindrical electrode portion; and wherein the circuit portion of the one or more electrodes further comprises a coupling structure for use in coupling the cylindrical electrode portion to the circuit portion, wherein the coupling structure of the circuit portion comprises at least one tongue element extending away from the axis, wherein the cylindrical electrode portion of the one or more electrodes defines at least one notch proximate the distal end corresponding to the at least one tongue element of the circuit portion, and wherein the tongue of the circuit portion is mechanically coupled within the at least one notch of the cylindrical electrode portion of the one or more electrodes.

* * * * *